US010584378B2

(12) United States Patent
Crnogorac et al.

(10) Patent No.: US 10,584,378 B2
(45) Date of Patent: Mar. 10, 2020

(54) METHODS FOR SYNCHRONIZING NUCLEIC ACID MOLECULES

(71) Applicant: Centrillion Technology Holdings Corporation, Grand Cayman (KY)

(72) Inventors: Filip Crnogorac, Redwood City, CA (US); Wei Zhou, Saratoga, CA (US)

(73) Assignee: Centrillion Technology Holdings Corporation, Grand Cayman (KY)

( * ) Notice: Subject to any disclaimer, the term of this patent is extended or adjusted under 35 U.S.C. 154(b) by 425 days.

(21) Appl. No.: 15/235,668

(22) Filed: Aug. 12, 2016

(65) Prior Publication Data
US 2017/0044601 A1  Feb. 16, 2017

Related U.S. Application Data

(60) Provisional application No. 62/204,942, filed on Aug. 13, 2015, provisional application No. 62/250,362, filed on Nov. 3, 2015, provisional application No. 62/254,647, filed on Nov. 12, 2015.

(51) Int. Cl.
*C12Q 1/68* (2018.01)
*C07H 21/00* (2006.01)
*C12Q 1/6869* (2018.01)
*C12Q 1/6874* (2018.01)

(52) U.S. Cl.
CPC ......... *C12Q 1/6869* (2013.01); *C12Q 1/6874* (2013.01)

(58) Field of Classification Search
CPC ......... C12Q 1/68; C12Q 1/6869; C07H 21/00
See application file for complete search history.

(56) References Cited

U.S. PATENT DOCUMENTS

| | | | |
|---|---|---|---|
| 4,683,202 A | 7/1987 | Mullis | |
| 4,883,750 A | 11/1989 | Whiteley et al. | |
| 5,143,854 A | 9/1992 | Pirrung et al. | |
| 5,302,509 A * | 4/1994 | Cheeseman | C12Q 1/6869 |
| | | | 435/6.11 |
| 5,470,705 A | 11/1995 | Grossman et al. | |
| 5,547,839 A | 8/1996 | Dower et al. | |
| 5,578,832 A | 11/1996 | Trulson et al. | |
| 5,631,734 A | 5/1997 | Stern et al. | |
| 5,644,048 A | 7/1997 | Yau | |
| 5,800,992 A | 9/1998 | Fodor et al. | |
| 5,834,758 A | 11/1998 | Trulson et al. | |
| 5,856,092 A | 1/1999 | Dale et al. | |
| 5,902,723 A | 5/1999 | Dower et al. | |
| 5,936,324 A | 8/1999 | Montagu | |
| 5,981,956 A | 11/1999 | Stern | |
| 6,025,601 A | 2/2000 | Trulson et al. | |
| 6,090,555 A | 7/2000 | Fiekowsky et al. | |
| 6,141,096 A | 10/2000 | Stern et al. | |
| 6,185,030 B1 | 2/2001 | Overbeck | |
| 6,201,639 B1 | 3/2001 | Overbeck | |
| 6,218,803 B1 | 4/2001 | Montagu et al. | |
| 6,225,625 B1 | 5/2001 | Pirrung et al. | |
| 7,689,022 B2 | 3/2010 | Weiner et al. | |
| 9,328,382 B2 | 5/2016 | Drmanac et al. | |
| 2003/0165861 A1 | 9/2003 | Wakabayashi et al. | |
| 2006/0147935 A1* | 7/2006 | Linnarsson | C12Q 1/6869 |
| | | | 435/6.1 |
| 2011/0014611 A1 | 1/2011 | Ju et al. | |
| 2012/0020537 A1 | 1/2012 | Garcia et al. | |
| 2012/0035062 A1* | 2/2012 | Schultz | C12Q 1/6874 |
| | | | 506/7 |
| 2012/0083417 A1 | 4/2012 | Zhou et al. | |
| 2013/0281306 A1 | 10/2013 | Rigatti et al. | |
| 2014/0186940 A1 | 7/2014 | Goel | |
| 2014/0315724 A1 | 10/2014 | Zhou et al. | |
| 2016/0046985 A1 | 2/2016 | Drmanac et al. | |
| 2016/0168632 A1 | 6/2016 | Edwards | |
| 2017/0022554 A1 | 1/2017 | Drmanac et al. | |

FOREIGN PATENT DOCUMENTS

| | | |
|---|---|---|
| WO | WO-9947964 A1 | 9/1999 |
| WO | WO-2011156707 A2 | 12/2011 |
| WO | WO-2012106546 A2 | 8/2012 |
| WO | WO-2012134602 A2 | 10/2012 |
| WO | WO-2012106546 A3 | 11/2013 |
| WO | WO-2015017759 A1 | 2/2015 |
| WO | WO-2017027783 A1 | 2/2017 |

OTHER PUBLICATIONS

Kircher et al., Addressing challenges in the production and analysis of illumina sequencing data. BMC Genomics 12 :382 (Year: 2011).*
Metzker, M. Sequencing technologies—the next generation. Nature Reviews | Genetics 11 :31 (Year: 2010).*
Guo et al.An Integrated System for DNA Sequencing by Synthesis Using Novel Nucleotide Analogues. Accounts of Chemical Research 43(4) : 551 (Year: 2010).*
Ronaghi, M., Pyrosequencing Sheds Light on DNA Sequencing. Genome Research 11 :3-11 (Year: 2001).*
EP16184099.6 Office Action dated Jan. 15, 2018.
European Search Report dated Dec. 16, 2016 for EP Application No. 16184099.6-1404.
Barany, F., Genetic disease detection and DNA amplification using cloned thermostable ligase.Proc Natl Acad Sci U S A. Jan. 1, 1991; 88(1): 189-193.
Grossman, et al., High-density multiplex detection of nucleic acid sequences: oligonucleotide ligation assay and sequence-coded separation.
Harris, et al., Single-molecule DNA sequencing of a viral genome. Science. Apr. 4, 2008;320(5872):106-9. doi: 10.1126/science. 1150427.

(Continued)

*Primary Examiner* — Ethan C Whisenant
(74) *Attorney, Agent, or Firm* — Centrillion Technology Holdings Corporation

(57) ABSTRACT

The methods, systems, kits and reagents provided herein relate to the synchronization of dephased/prephased nucleic acid molecules during sequencing reactions. The methods, systems, kits and reagents provided herein can be utilized to improve the efficiency and accuracy of sequencing technologies.

17 Claims, 24 Drawing Sheets

Specification includes a Sequence Listing.

(56) References Cited

OTHER PUBLICATIONS

Landegren, et al., A ligase-mediated gene detection technique. Science. Aug. 26, 1988;241(4869):1077-80.
Nickerson, et al., Automated DNA diagnostics using an ELISA-based oligonucleotide ligation assay.Proc Natl Acad Sci U S A. Nov. 1990;87(22):8923-7.
Ju, et al., Four-color DNA sequencing by synthesis using cleavable fluorescent nucleotide reversible terminatiors. PNAS. Dec. 2006. 103(52):19635-19640.
Minoche, et al., Evaluation of genomic high-througput sequencing data generated on illumina hiseq and genome analyzer systems. Genome Biology, 2011.15:R112.
Ronaghi, M. Pyrosequencing Sheds light on DNA sequencing. Cold spring harbor laboratory press. 2016.
Wicker, et al. 454 Sequencing put to the test using the complex genome of barley. BMC Genomic. Oct. 2006.7:275.
International Search Report and Written Opinion dated Dec. 12, 2016 for International Application PCT/US2016/046711.
EP16184099.6 Office Action dated Oct. 2, 2018.

\* cited by examiner

Results of multiple +S cycles:

| | Average Synch. | COMPLETELY (100%) in SYNC |
|---|---|---|
| 1 +S cycle (ACGT): | 96.5% | 70% of clusters |
| 2 +S cycles (ACGTACGT): | 97.2% | 75% of clusters |
| 3 +S cycles (ACGTACGTACGT): | 97.3% | 76% of clusters |
| 4 +S cycles (ACGTACGTACGTACGT): | 97.3% | 76% of clusters |

FIG. 6

| Step | Length(bp) | Dark Base | Sequence |
|---|---|---|---|
| 1 | 7 | GCT | GGCTCTC |
| 2 | 14 | AGC | GGCTCTCAAGGGCA |
| 3 | 21 | TCG | GGCTCTCAAGGGCATCGGTCG |
| 4 | 28 | ACG | GGCTCTCAAGGGCATCGGTCGACGC |
| 5 | 35 | TCA | GGCTCTCAAGGGCATCGGTCGACGCTCTCCCTTAT |
| 6 | 40 | GCA | GGCTCTCAAGGGCATCGGTCGACGCTCTCCCTTATGCGAC |
| 7 | 46 | TCG | GGCTCTCAAGGGCATCGGTCGACGCTCTCCCTTATGCGACTCGTGC |
| 8 | 55 | ATG | GGCTCTCAAGGGCATCGGTCGACGCTCTCCCTTATGCGACTCGTGCATTAGGAAG |
| 9 | 63 | CAG | GGCTCTCAAGGGCATCGGTCGACGCTCTCCCTTATGCGACTCGTGCATTAGGAAGCAGCCCAAG |
| 10 | 76 | ATG | GGCTCTCAAGGGCATCGGTCGACGCTCTCCCTTATGCGACTCGTGCATTAGGAAGCAGCCCAAGTAGTAGGTAGGTGAGG |
| 11 | 82 | GCT | GGCTCTCAAGGGCATCGGTCGACGCTCTCCCTTATGCGACTCGTGCATTAGGAAGCAGCCCAAGTAGTAGGTAGGTGAGGCCGTTG |
| 12 | 103 | AGC | GGCTCTCAAGGGCATCGGTCGACGCTCTCCCTTATGCGACTCGTGCATTAGGAAGCAGCCCAAGTAGTAGGTAGGTGAGGCCGTTGAGCACCGCCCGTCAAGGAA |

FIG. 7

Modeling Optimal Extension for *Inline 'S*

Given typical phasing after 150 cycles of SBS, we modeled the *Inline 'S* to find the optimal number and combination of triplets extensions which would yield the best strand synchronization.

Results of simulation testing synchronization of 100,000 random DNA sequences (clusters), with an pre-phasing distribution at 150 SBS cycles given by the empirical model (Ver2):

| Number tested | Triplet Combinations | (i.e. -C, -G, -T, +A) | Average synchronization |
|---|---|---|---|
| No *Inline 'S* extensions | Control | | 80.2% |
| 4 *Inline 'S* extensions | A, C, G, T | | 98.5% |
| 8 *Inline 'S* extensions | A, C, G, T, A, C, G, T | | 97.2% |
| 12 *Inline 'S* extensions | A, C, G, T, A, C, G, T, A, C, G, T | | 97.5% |
| 16 *Inline 'S* extensions | A, C, G, T, A, C, G, T, A, C, G, T, A, C, G, T | | 97.5% |

Increasing *Inline 'S* extensions past 8 has diminishing returns. Then, optimizing the triplet order:

| Optimal Method | Triplet Combinations | (i.e. -A, -C, -G, -T) | Average synchronization |
|---|---|---|---|
| 8 *Inline 'S* extensions | A, C, G, T, G, C, A, T | | 98.7% |

Optimal method of 8 extensions (-A, -C, -G, -T, -G, -C, -A, -T) yields a maximum average synchronization of 98.7%, i.e. in an average cluster, 98.7% of DNA strands are synchronized to the exact same position.

Modeled average total extension length of optimal 8 *Inline 'S* steps is 33.5 ± 10 bp Notes: clusters that do not fully synchronize have 'X' in position 149, and ACGT as the first ~10 bases after. This would prevent the phased DNA strands from catching up to the majority during *Inline 'S*.

FIG. 20

METHODS FOR SYNCHRONIZING NUCLEIC ACID MOLECULES

CROSS-REFERENCE

This application claims the benefit of U.S. Provisional Application No. 62/204,942, filed Aug. 13, 2015, U.S. Provisional Application No. 62/250,362, filed Nov. 3, 2015, and U.S. Provisional Application No. 62/254,647, filed Nov. 12, 2015, which applications are each incorporated herein by reference.

SEQUENCE LISTING

The instant application contains a Sequence Listing which has been submitted electronically in ASCII format and is hereby incorporated by reference in its entirety. Said ASCII copy, created on Dec. 13, 2018, is named 38558-726_601_SL.txt and is 4,445 bytes in size.

BACKGROUND OF THE INVENTION

Nucleic acid sequencing is important for biological research, clinical diagnostics, personalized medicine and pharmaceutical development and many other fields. Cost effective, accurate and fast sequencing is needed for many applications, such as, but not limited to for microbial or pathogen detection and identification, and genetic identification for subjects. For example, applications can include, but not be limited to paternity testing and in forensic science (Reynolds et al., Anal. Chem., 63:2-15 (1991)), for organ-transplant donor-recipient matching (Buyse et al., Tissue Antigens, 41:1-14 (1993) and Gyllensten et al., PCR Meth. Appl, 1:91-98 (1991)), for genetic disease diagnosis, prognosis, and pre-natal counseling (Chamberlain et al., Nucleic Acids Res., 16:11141-11156 (1988) and L. C. Tsui, Human Mutat., 1:197-203 (1992)), and the study of drug metabolism and oncogenic mutations (Hollstein et al., Science, 253:49-53 (1991)). In addition, the cost-effectiveness of nucleic acid analysis, such as for infectious disease diagnosis, varies directly with the multiplex scale in panel testing. Many of these applications depend on the discrimination of single-base differences at a multiplicity of sometimes closely spaced loci.

A variety of DNA hybridization techniques are available for detecting the presence of one or more selected polynucleotide sequences in a sample containing a large number of sequence regions. In a simple method, which relies on fragment capture and labeling, a fragment containing a selected sequence is captured by hybridization to an immobilized probe. The captured fragment can be labeled by hybridization to a second probe which contains a detectable reporter moiety.

Another widely used method is Southern blotting. In this method, a mixture of DNA fragments in a sample is fractionated by gel electrophoresis, and then fixed on a nitrocellulose filter. By reacting the filter with one or more labeled probes under hybridization conditions, the presence of bands containing the probe sequences can be identified. The method is especially useful for identifying fragments in a restriction-enzyme DNA digest which contains a given probe sequence and for analyzing restriction-fragment length polymorphisms ("RFLPs").

Another approach to detecting the presence of a given sequence or sequences in a polynucleotide sample involves selective amplification of the sequence(s) by polymerase chain reaction, U.S. Pat. No. 4,683,202 and R. K. Saiki, et al., Science 230:1350 (1985). In this method, primers complementary to opposite end portions of the selected sequence(s) are used to promote, in conjunction with thermal cycling, successive rounds of primer-initiated replication. The amplified sequence(s) may be readily identified by a variety of techniques. This approach is particularly useful for detecting the presence of low-copy sequences in a polynucleotide-containing sample, e.g., for detecting pathogen sequences in a body-fluid sample.

More recently, methods of identifying known target sequences by probe ligation methods have been reported, U.S. Pat. No. 4,883,750, D. Y. Wu, et al., Genomics 4:560 (1989), U. Landegren, et al., Science 241:1077 (1988), and E. Winn-Deen, et al., Clin. Chem. 37:1522 (1991). In one approach, known as oligonucleotide ligation assay ("OLA"), two probes or probe elements which span a target region of interest are hybridized to the target region. Where the probe elements basepair with adjacent target bases, the confronting ends of the probe elements can be joined by ligation, e.g., by treatment with ligase. The ligated probe element is then assayed, evidencing the presence of the target sequence.

In a modification of this approach, the ligated probe elements act as a template for a pair of complementary probe elements. With continued cycles of denaturation, hybridization, and ligation in the presence of pairs of probe elements, the target sequence is amplified linearly, allowing very small amounts of target sequence to be detected and/or amplified. This approach is referred to as ligase detection reaction. When two complementary pairs of probe elements are utilized, the process is referred to as the ligase chain reaction which achieves exponential amplification of target sequences. F. Barany, Proc. Nat'l Acad. Sci. USA, 88:189-93 (1991) and F. Barany, PCR Methods and Applications, 1:5-16 (1991).

Another scheme for multiplex detection of nucleic acid sequence differences is disclosed in U.S. Pat. No. 5,470,705 where sequence-specific probes, having a detectable label and a distinctive ratio of charge/translational frictional drag, can be hybridized to a target and ligated together. This technique was used in Grossman, et al., Nucl. Acids Res. 22(21):4527-34 (1994) for the large scale multiplex analysis of the cystic fibrosis transmembrane regulator gene. Jou, et al., Human Mutation 5:86-93 (1995) relates to the use of a so called "gap ligase chain reaction" process to amplify simultaneously selected regions of multiple exons with the amplified products being read on an immunochromatographic strip having antibodies specific to the different haptens on the probes for each exon.

Ligation of allele-specific probes generally has used solid-phase capture (U. Landegren et al., Science, 241:1077-1080 (1988); Nickerson et al., Proc. Natl. Acad. Sci. USA, 87:8923-8927 (1990)) or size-dependent separation (D. Y. Wu, et al., Genomics, 4:560-569 (1989) and F. Barany, Proc. Natl. Acad. Sci, 88:189-193 (1991)) to resolve the allelic signals, the latter method being limited in multiplex scale by the narrow size range of ligation probes. Further, in a multiplex format, the ligase detection reaction alone cannot make enough product to detect and quantify small amounts of target sequences. The gap ligase chain reaction process requires an additional step—polymerase extension. The use of probes with distinctive ratios of charge/translational frictional drag for a more complex multiplex will either require longer electrophoresis times or the use of an alternate form of detection.

Methods for efficiently and accurately sequencing long nucleic acid fragments are needed. There is a great need for rapid, high-throughput, and low cost sequencing technology, such as for point-of-care applications and field detection of pathogens. The present invention permits sequencing of large amount of genome using simple chemistry and low cost equipment that lead to significant cost reduction and increase in speed, and other related advantages as well.

SUMMARY OF THE INVENTION

In one aspect, a sequencing-by-synthesis (SBS) system is provided, wherein the system is configured to produce sequencing reads greater than at least 300 base pairs having a chastity score of at least 0.85 or greater. The system may be configured to produce sequencing reads greater than at least 100 kB having a chastity score of at least 0.85 or greater.

In another aspect, a method for sequence determination is provided, the method comprising: performing a sequencing-by-synthesis (SBS) reaction to generate sequencing reads greater than 300 base pairs having a chastity score of at least 0.85 or greater. The method may comprise performing a sequencing-by-synthesis reaction to generate sequencing reads greater than at least 100 kB having a chastity score of at least 0.85 or greater.

In another aspect, a method of improving a chastity score of a sequencing reaction is provided, the method comprising: performing one or more synchronization steps on a plurality of sequencing products, wherein the chastity score is improved by at least 20% relative to a corresponding sequencing reaction performed in the absence of one or more synchronization steps. In some cases, the plurality of sequencing products comprises one or more unsynchronized sequencing products. Each of the one or more synchronization steps may comprise: extending the plurality of sequencing products in the presence of a set of up to three different nucleotides. In some cases, the up to three different nucleotides are selected from the group consisting of: dATP, dCTP, dGTP, dTTP and dUTP. In some cases, the up to three different nucleotides comprise at least one native nucleotide. The method may further comprise, prior to performing the one or more synchronization steps, performing one or more successive rounds of sequencing, wherein each round of sequencing comprises (i) extending a plurality of sequencing primers using a plurality of target nucleic acids as template in the presence of one or more labeled nucleotides to generate the plurality of sequencing products; and (ii) determining a nucleic acid sequence for each of the plurality of sequencing products. The method may further comprise, prior to performing the one or more successive rounds of sequencing, hybridizing the plurality of sequencing primers to the plurality of target nucleic acids. The method may further comprise, after performing the one or more synchronization steps, repeating, one or more times, one or more rounds of sequencing followed by one or more synchronization steps. In some cases, after the repeating, the sequencing reaction having a chastity score of at least 0.85. The method of improving a chastity score may comprise performing at least four synchronization steps. The method of improving a chastity score may comprise performing at least eight synchronization steps. The performing one or more successive rounds of sequencing may comprise performing from 100 to 200 successive rounds of sequencing. In some cases, the plurality of target nucleic acids are immobilized to a solid support via a capture probe. The method may further comprise, removing the set of up to three different nucleotides after each synchronization step (i) by washing or (ii) by the use of a nucleotide degrading enzyme. In some cases, the extending comprises extending with the use of a DNA polymerase.

In another aspect, a method is provided for improving a length of accurate base calls in a sequencing read of a sequencing reaction, the method comprising performing one or more synchronization steps on a plurality of sequencing products, thereby increasing the length of accurate base calls in the sequencing read of the sequencing reaction. In some cases, the length of accurate base calls in the sequencing read of the sequencing reaction is increased by at least 10 base pairs as compared to a length of accurate base calls in a sequencing read of a sequencing reaction performed in the absence of one or more synchronization steps. In some cases, the length of accurate base calls in the sequencing read of the sequencing reaction is increased by at least 50 base pairs as compared to a length of accurate base calls in a sequencing read of a sequencing reaction performed in the absence of one or more synchronization steps. In some cases, the length of accurate base calls in the sequencing read of the sequencing reaction is increased by at least 100 to 500 base pairs as compared to a length of accurate base calls in a sequencing read of a sequencing reaction performed in the absence of one or more synchronization steps. Each of the one or more synchronization steps may comprise extending the plurality of sequencing products in the presence of a set of up to three different nucleotides. In some cases, the up to three different nucleotides are selected from the group consisting of: dATP, dCTP, dGTP, dTTP and dUTP. In some cases, the plurality of sequencing products comprises one or more unsynchronized sequencing products. In some cases, a chastity score of the sequencing products is at least 0.85 after the one or more synchronization steps. In some cases, the up to three different nucleotides comprises at least one native nucleotide. The method may further comprise, prior to performing the one or more synchronization steps, performing one or more successive rounds of sequencing, wherein each round of sequencing comprises (i) extending a plurality of sequencing primers using a plurality of target nucleic acids as template in the presence of one or more labeled nucleotides to generate the plurality of sequencing products; and (ii) determining a nucleic acid sequence for each of the plurality of sequencing products. The method may further comprise, prior to performing the one or more successive rounds of sequencing, hybridizing the plurality of sequencing primers to the plurality of target nucleic acids. The method may further comprise, after performing the one of more synchronization steps, repeating, one or more times, one or more rounds of sequencing followed by one or more synchronization steps. In some cases, after the repeating, the sequencing reaction having a chastity score of at least 0.85. In some cases, the method of improving a length of accurate base calls comprises performing at least four synchronization steps. In some cases, the method of improving a length of accurate base calls comprises performing at least eight synchronization steps. In some cases, the performing one or more successive rounds of sequencing comprises performing from 100 to 200 successive rounds of sequencing. In some cases, the plurality of target nucleic acids are immobilized to a solid support via a capture probe. The method may further comprise, removing the set of up to three different nucleotides after each synchronization step (i) by washing or (ii) by the use of a nucleotide degrading enzyme. In some cases, the extending comprises extending with the use of a DNA polymerase.

In yet another aspect, a method is provided for synchronizing one or more unsynchronized sequencing products, the method comprising: (a) performing one or more synchronization steps on a plurality of sequencing products, the plurality of sequencing products comprising the one or more unsynchronized sequencing products, wherein each of the one or more synchronization steps comprises: (i) contacting the plurality of sequencing products with a first set of up to three different nucleotides selected from the group consisting of: dATP, dTTP, dCTP, dGTP and dUTP; (ii) extending the plurality of sequencing products with a DNA polymerase; and (iii) optionally, removing the set of unlabeled nucleotides, thereby synchronizing the one or more unsynchronized sequencing products. In some cases, each consecutive synchronization step of the one or more synchronization steps comprises: contacting the plurality of sequencing products with a second set of up to three different nucleotides selected from the group consisting of: dATP, dTTP, dCTP, dGTP and dUTP, wherein the second set of nucleotides is different from the first set of nucleotides. The method may further comprise, prior to performing the one or more synchronization steps: (b) hybridizing a plurality of sequencing primers to a plurality of target nucleic acids; and (c) performing one or more successive rounds of sequencing, each round of sequencing comprising: (i) extending the plurality of sequencing primers in the presence of one or more labeled nucleotides to generate the plurality of sequencing products; and (ii) determining a nucleic acid sequence of the plurality of sequencing products. In some cases, the performing one or more successive rounds of sequencing comprises performing from 100 to 200 successive rounds of sequencing. The method may further comprise, The method of claim 41, further comprising, after performing the one or more synchronization steps, repeating, one or more time, the one or more successive rounds of sequencing followed by the one or more synchronization steps. In some cases, the set of up to three different nucleotides further comprises a reversible terminator nucleotide. In some cases, after each synchronization step, the reversible terminator nucleotide is deblocked and the plurality of sequencing products are made ready for further extension. In some cases, the reversible terminator nucleotide has a different base than the up to three different nucleotides within each set. In some cases, the method of synchronizing one or more unsynchronized sequencing products comprises performing at least four synchronization steps. In some cases, the method of synchronizing one or more unsynchronized sequencing products comprises performing at least eight synchronization steps. In some cases, after performing the one or more synchronization steps, at least 95% of the sequencing products are synchronized. In some cases, after performing the one or more synchronization steps, the sequencing products having a chastity score of at least 0.85. In some cases, the plurality of target nucleic acids are attached to a solid support via a capture probe. The method may further comprise, removing the set of up to three different nucleotides after each synchronization step (i) by washing or (ii) by the use of a nucleotide degrading enzyme. In some cases, the set of up to three different nucleotides comprises native nucleotides. In some cases, the one or more labeled nucleotides comprises one or more fluorescently-labeled nucleotides.

In another aspect, a kit is provided for sequencing a target nucleic acid molecule, the kit comprising: (a) a primer hybridizable to the target nucleic acid molecule, (b) one or more labeled nucleotides; and (c) one or more sets of up to three different nucleotides selected from the group consisting of: dATP, dTTP, dCTP, dGTP and dUTP. The kit may further comprise a DNA polymerase. The kit may further comprise a pyrophosphatase. The kit may further comprise an apyrase. In some cases, the one or more labeled nucleotides comprises one or more fluorescently-labeled nucleotides. In some cases, the one or more sets of up to three different nucleotides comprises at least one of the sets selected from the group consisting of: a set comprising dATP, dCTP and dGTP; a set comprising dATP, dTTP and dGTP; a set comprising dCTP, dGTP and dTTP, a set comprising dATP, dCTP and dTTP; and any combination thereof. In some cases, the one or more sets of up to three different nucleotides further comprises a reversible terminator nucleotide. In some cases, the reversible terminator nucleotide comprises a different base than the up to three different nucleotides within each set.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 compares the use of multiple synchronization cycles to resynchronize sequencing strands in a cluster. FIG. 6 discloses SEQ ID NOS 1-2, respectively, in order of appearance.

FIG. 7 depicts the incorporation of dark nucleotide sets into a sequencing product. FIG. 7 discloses SEQ ID NOS 3-13, respectively, in order of appearance.

FIG. 18 discloses SEQ ID NOS 14, 14, 14, 14, 15, 14, and 16, respectively, in order of appearance.

FIG. 19 discloses SEQ ID NOS 14, 14, 14, 14, 15, 14, and 16, respectively, in order of appearance.

FIG. 20 depicts an example of a method described herein.

DETAILED DESCRIPTION OF THE INVENTION

Figure 1:
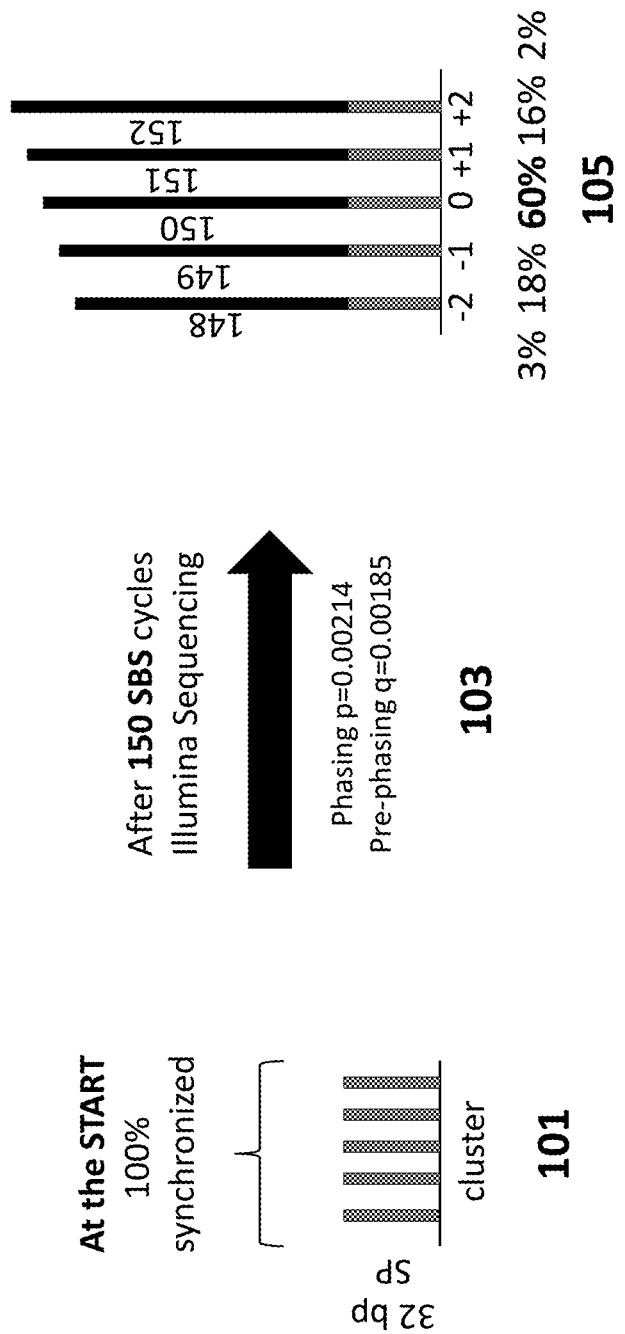
FIG. 1 depicts signal deterioration using sequencing-by-synthesis (SBS) methods.
Figure 2:
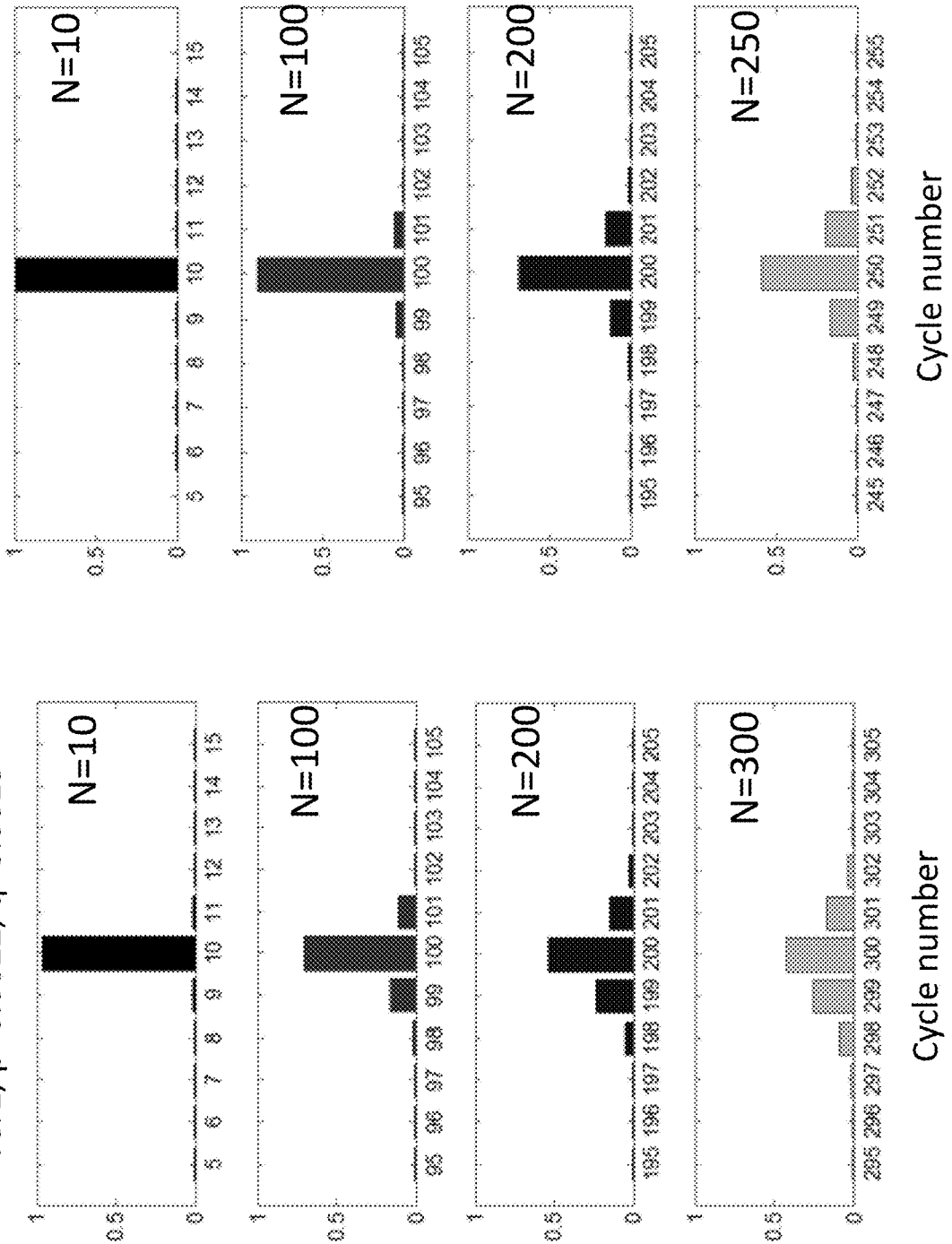
FIG. 2 depicts dephasing of an initially in-sync clonal cluster after 150 SBS cycles

Unless defined otherwise, all technical and scientific terms used herein have the same meaning as commonly understood by one of ordinary skill in the art to which this present invention belongs. Although any methods and materials similar or equivalent to those described herein can also be used in the practice or testing of the present invention, representative illustrative methods and materials are now described. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press); Stryer, L. (1995) Biochemistry (4th Ed.) Freeman, New York; Gait, "Oligonucleotide Synthesis: A Practical Approach" 1984, IRL Press, London, Nelson and Cox (2000), Lehninger, (2004) Principles of Biochemistry $4^{th}$ Ed., W. H. Freeman Pub., New York, N.Y. and Berg et al. (2006) Biochemistry, 6th Ed., W. H. Freeman Pub., New York, N.Y., all of which are herein incorporated in their entirety by reference for all purposes.

In one aspect of the invention, methods, kits, computer software products are provided for sequencing long nucleic acids. Nucleic acids are often sequenced using stepwise methods such as polymerase extension based sequencing or ligation sequencing, where one or more bases are read for each sequencing step. These stepwise based sequencing methods are often limited by their stepwise inefficiency, e.g., incomplete incorporation, incomplete ligation and other problems that create prephasing or dephasing. The stepwise inefficiency can accumulate over read length and limits read length.

For example, reversible terminator nucleotide based sequencing (commercially available from Helicos, Inc., Illumina, Inc., Intelligent Biosystems, Inc./Azco Biotech, Inc. and described in vendor literature and their patent filings and at http://www.helicosbio.com, http://www.illumina.com, http://www.azcobiotech.com) are limited by the efficiency of incorporating reversible terminator nucleotides that are modified in the 3' hydroxyl group or modified otherwise to interrupt further extension by a polymerase. If the sequencing detection is based upon incorporation of modified nucleotides with added detectable label such as a fluorescent group, the incorporation efficiency could be further reduced. The problem can be partially alleviated by mixing unlabeled and labeled reversible terminator nucleotides. However, even with improved chemistry and efficiency, the stepwise inefficiency can significantly limit read length and read quality at the end of the read.

The stepwise efficiency problem can be illustrated with a case where each sequencing step has a constant stepwise efficiency of incorporation of about 99% and there are 1,000 template molecules in a cluster. After the first incorporation step, 10 sequencing primers are not extended and are capped or otherwise no longer involved in sequencing. In such a case, after 100 sequencing steps, only $(0.99)^{100}=36.6\%$ or 360 molecules remain in the cluster for additional sequencing. At step 200, only $(0.99)^{200}=13.4\%$ or 134 molecules remain in the cluster for additional sequencing. If the efficiency drops to 98%, at step 100, there are only 13.4% molecules left for additional sequencing reactions and at step 200, only 1.8% molecules can be potentially used for further sequencing.

For nucleotide limited addition sequencing methods such as pyrophosphate detection based sequencing (commercially available from Roche/454 and described in vendor literature and patent filings and at http:www.454.com) or pH detection based sequencing (commercially available from Ion Torrent, Inc./Life Technologies, Inc. and described in vendor literature and patent filings), the efficiency can be limited by incomplete incorporation, mis-incorporation, loss of bound polymerase (fall-off). Stepwise ligation based sequencing has a similar efficiency problem as stepwise efficiency is limited by, e.g., ligation reaction efficiency and removal of labels.

Additionally, step-wise sequencing methods can generate unsynchronized sequencing strands within a cluster of sequencing strands. This problem can limit the length of sequencing reads that can be achieved. As the sequencing products in a cluster are extended, due to inefficiencies of the sequencing reaction, one or more sequencing strands in the cluster may become unsynchronized with the other sequencing strands. FIG. 1 highlights this problem. At the start of a sequencing reaction, after hybridization of the sequencing primer, 100% of the strands within the cluster are synchronized. As the strands are extended, individual strands may fall behind or extend faster than the majority of the strands. This loss of synchronization is amplified as the number of sequencing rounds increases and eventually, the background noise from the unsynchronized strands becomes too great to accurately call the correct base. Using FIG. 1 as an example, a cluster may start with 100% of the strands synchronized 101, but after 150 SBS cycles 103, only 60% of the strands may be synchronized (i.e., only 60% of the signal is correct) 105. In this example, some of the strands will be behind (e.g., −1, −2, etc.) and some of the strands will be ahead (e.g., +1, +2, etc.). The methods provided herein, then, may be suitable to resynchronize (or reset) the strands, such that 100% or near 100% of the strands that were previously unsynchronized are synchronized. In some cases, the methods may be suitable to resynchronize a cluster of sequencing strands such that 80%, 85%, 90%, 91%, 92%, 93%, 94%, 95%, 96%, 97%, 98%, 99% or more than 99% of the sequencing strands that were previously unsynchronized are synchronized.

Figure 3:
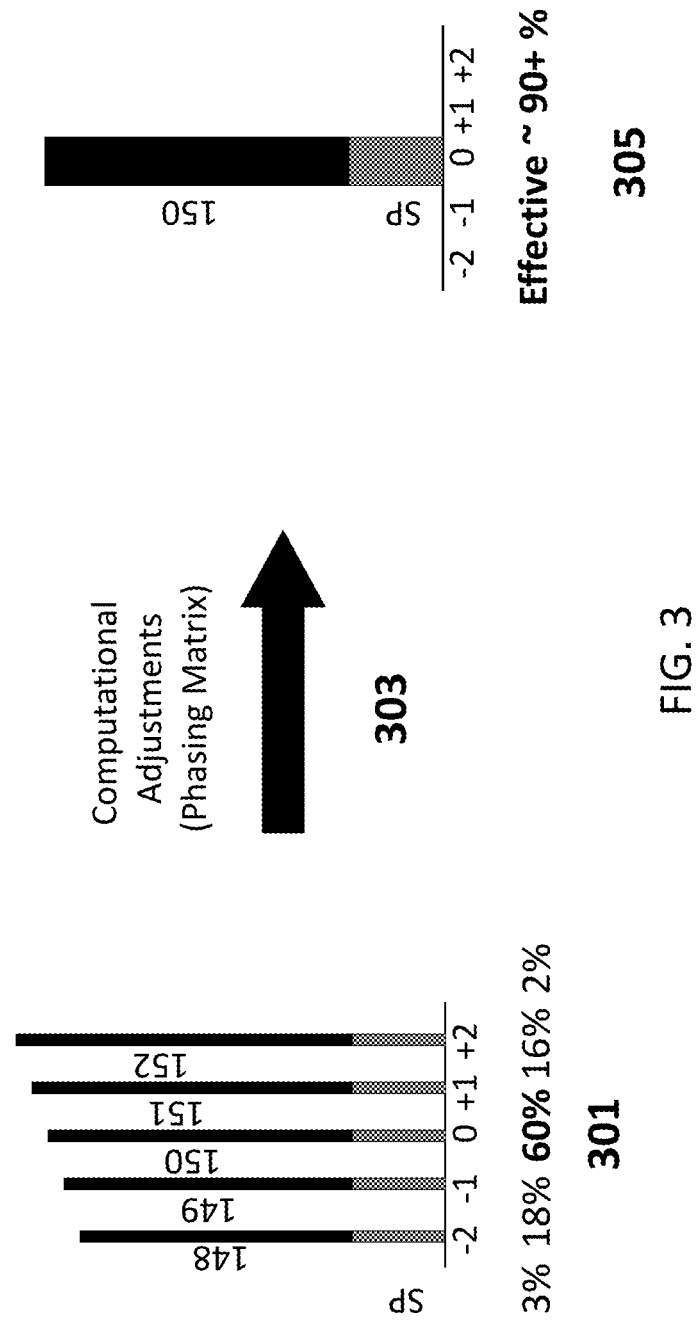
FIG. 3 depicts a computational method of resynchronizing sequencing strands in a cluster.

Current methods of resynchronizing strands in a cluster are generally performed in sit/co by, for example, software (e.g., algorithm). For example, as depicted in FIG. 3, computational methods can be utilized to resynchronize a cluster of unsynchronized strands. However, these methods are limited and may be only ~90% effective. These methods are performed computationally, and not by chemistry, and as such, the strands within a cluster are not physically synchronized. The present invention seeks to solve this problem by chemically resynchronizing the strands in a cluster. In some cases, the methods provided herein involve resynchronizing the strands in a cluster without the use of a computer (i.e., by chemistry). It should be understood that a computer may, however, be used in any step of the disclosure, such as any sequencing steps, calculating steps (i.e., calculating a chastity score), imaging steps, and the like.

Methods

The methods provided herein include one or more synchronization steps to resynchronize or reset a plurality of unsynchronized strands in a cluster. In some aspects of the invention, the one or more synchronization steps includes one or more extension steps wherein a plurality of sequencing products are extended in the presence of incomplete sets of nucleotides. In some cases, the incomplete sets of nucleotides contain up to three different nucleotides. For example, the set of nucleotides comprises one to three of the four types of nucleotides (e.g., for DNA polymerase, one, two or three of the four nucleotides dATP, dCTP, dTTP and dGTP). In some cases, the set of nucleotides may include dUTP. In some cases, a reaction containing three of the different nucleotides will stop at the template base that is complementary to the missing nucleotide. For example, for a reaction that has dATP, dCTP and dGTP, the extension stops at a base "A" on the template because "A" is complementary to the missing nucleotide dTTP, thereby limiting extension of the sequencing product. Examples of incomplete nucleotide sets that can be used to perform the methods herein are (also referred to by the missing nucleotide): dATP, dCTP and dGTP (-T); dCTP, dGTP and dTTP (-A); dATP, dCTP, and dTTP (-G); and dATP, dTTP, and dGTP (-C). Alternatively, nucleotide sets may be used that include three native, unlabeled nucleotides ("dark" nucleotides) and a reversible terminator nucleotide. In this example, the reversible terminator will be a nucleotide that is not represented by the three native nucleotides. The addition of a reversible terminator nucleotide to a sequencing product will prevent further elongation of the sequencing product until the terminator is removed.

In one aspect of the invention, methods are provided to synchronize a plurality of strands within a cluster. The method includes one or more successive rounds of sequencing in which nucleotides are incorporated into a growing sequencing strand (e.g., with the use of a polymerase). The method includes hybridizing a sequencing primer to a plurality of target nucleic acids. The target nucleic acids may be immobilized on a solid support. The method further includes performing one or more successive rounds of sequencing. Each of the one or more successive rounds of sequencing steps may include extending the sequencing primer in the presence of one or more labeled nucleotides to generate a sequencing product. The method may further include determining the nucleic acid sequence of the sequencing product. After the one or more rounds of sequencing, the method may further include performing one or more synchronization steps. The one or more synchronization steps may include extending the sequencing product in the presence of a set of up to three different nucleotides selected from the group consisting of: dATP, dTTP, dCTP and dGTP. In some cases, the set of up to three different nucleotides are unlabeled (e.g., native nucleotides).

In one aspect, the methods provided herein include performing a sequencing cycle followed by a synchronization cycle. The one or more rounds of sequencing may be collectively referred to herein as a "sequencing cycle", whereas the one or more synchronization steps may be collectively referred to herein as a "synchronization cycle." For example, a sequencing cycle may include one or more successive rounds of sequencing, in some cases from 100 to 200 sequencing steps. A synchronization cycle may include one or more synchronization steps, in some cases from four to eight synchronization steps. In some cases, the methods provide for performing one or more additional sequencing cycles followed by one or more additional synchronization cycles. For example, the methods include performing an additional sequencing cycle followed by an additional synchronization cycle one, two, three, four, five, six, seven, eight, nine, 10 or more than 10 times. Each synchronization cycle can reset or resynchronize the strands in a cluster.

In some cases, the method involves performing an additional sequencing cycle followed by an additional synchronization cycle one or more times. In some cases, the additional sequencing and synchronization cycles are different from the previous sequencing and synchronization cycles (e.g., each cycle may include a different number of steps). In other cases, the additional sequencing and synchronization cycles may be the same as the previous sequencing and synchronization cycles (i.e., each cycle includes the same number of steps). Each synchronization cycle may resynchronize at least 95% of the sequencing products in a sequencing cluster. In a non-limiting example, the sequencing cycle includes about 150 sequencing steps and the synchronization cycle includes about eight synchronization steps.

Figure 4:
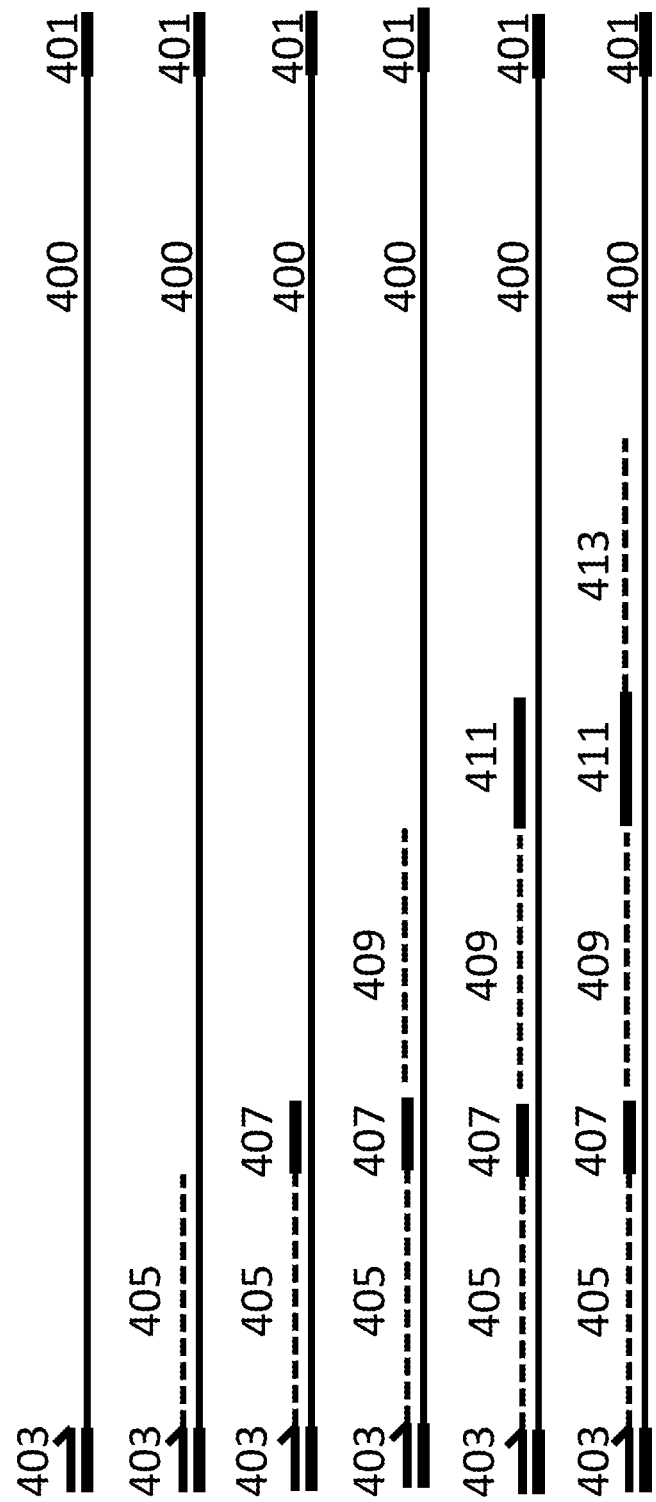
FIG. 4 depicts an example of utilizing methods of the disclosure for resynchronizing sequencing strands in a cluster.

FIG. 4 depicts an example of the methods provided herein in a step-wise fashion. In this example, in the first step (from the top), a target nucleic acid 400 may hybridize to a capture probe 401 (e.g., on a solid support). A sequencing primer 403 can be hybridized to the target nucleic acid 401 and a sequencing cycle can be performed to generate a sequencing product 405. Following the sequencing cycle, a synchronization cycle may be performed to resynchronize the sequencing product 407. An additional sequencing cycle is then performed to further extend the sequencing product 409 and generate a sequencing read. The additional sequencing cycle is then followed by an additional synchronization cycle to resynchronize the sequencing products 411 followed by an additional sequencing cycle 413 and so forth. The additional sequencing cycle followed by an additional synchronization cycle can be repeated as many times as necessary to sequence the entire target nucleic acid. The number of sequencing rounds in a sequencing cycle may be determined empirically. Without wishing to be bound by theory, each sequencing round generally results in a slight loss of signal intensity until enough sequencing rounds have been performed that the loss of signal intensity is too great to accurately call the correct base. At this point, it may be suitable to perform a synchronization cycle to reset or resynchronize the strands and restore the loss of signal. Although the optimal number of sequencing rounds in a sequencing cycle will vary, it is contemplated that enough sequencing rounds will be performed to result in a loss of synchronization of the sequencing strands before a synchronization cycle is performed. The loss of synchronization of the sequencing strands may include about 50%, 55%, 60%, 65%, 70%, 75%, 80%, 85%, 90%, 95%, up to 100% unsynchronized strands in a cluster. In some cases, the number of sequencing rounds in a sequencing cycle is 50 or more. In some examples, the number of sequencing rounds in a sequencing cycle are 100 or more. Non-limiting examples include about 100, about 110, about 120, about 130, about 140, about 150, about 160, about 170, about 180, about 190, about 200 or more than 200 sequencing rounds in a sequencing cycle. In some cases, the rounds of sequencing include from 100 to 200 sequencing rounds.

The number of synchronization steps in a synchronization cycle can also be determined empirically. In some cases, the number of synchronization steps in a synchronization cycle may include, without limitation: one, two, three, four, five, six, seven, eight, nine, ten or ten or more synchronization steps. In some cases, one or more synchronization steps are performed in a synchronization cycle. In some cases, four or more synchronization steps are performed in a synchronization cycle. In other cases, eight or more synchronization steps are performed in a synchronization cycle. In some cases, from four to eight synchronization steps are performed in a synchronization cycle.

The order of synchronization steps can also be determined empirically. In some cases, each consecutive synchronization step includes a different set of incomplete nucleotides. For example, a synchronization step performed in the absence of dATP ("-A"; i.e., in the presence of dTTP, dCTP and dGTP) may be followed up with a synchronization step with one of the nucleotide sets: "-T", "-C", or "-G". In a non-limiting example, a synchronization cycle includes eight synchronization steps performed in the following order: "-A", "-C", "-G", "-T", "-G", "-C", "-A", "-T". Synchronization steps can include a set of up to three different nucleotides. The up to three different nucleotides may be unlabeled nucleotides. An unlabeled nucleotide may be any nucleotide that is free of a detectable label. In some cases, the unlabeled nucleotides are "dark" nucleotides (i.e., absent of a detectable, e.g., fluorescent, label). In some cases, the unlabeled nucleotides are native nucleotides and do not contain any modifications. In some cases, the unlabeled nucleotides are modified nucleotides (e.g., contain a reversible terminator).

The use of unlabeled nucleotides during the synchronization steps can result in the absence of sequencing data for a plurality of nucleotide positions on a template nucleic acid. Each synchronization step can result in the extension of a sequencing product by about, on average, three, four, five, six, seven, eight, nine, ten or more nucleotides. In some cases, about four nucleotides, on average, may be added to a sequencing product at each synchronization step. FIG. 7 depicts an example of the addition of "dark" (i.e., unlabeled) nucleotides to a sequencing product using a plurality of synchronization steps. Each synchronization step in this example can add roughly seven unlabeled nucleotides to a sequencing product, such that after 12 synchronization steps, about 102 unlabeled nucleotides are added to the sequencing product. The absence of a detectable label will result in a gap of unsequenced bases on a sequencing product. By staggering the number of sequencing steps performed prior to synchronization (e.g., 100 sequencing steps versus 150 sequencing steps), the gaps in the sequencing data could be filled.

Figure 5:
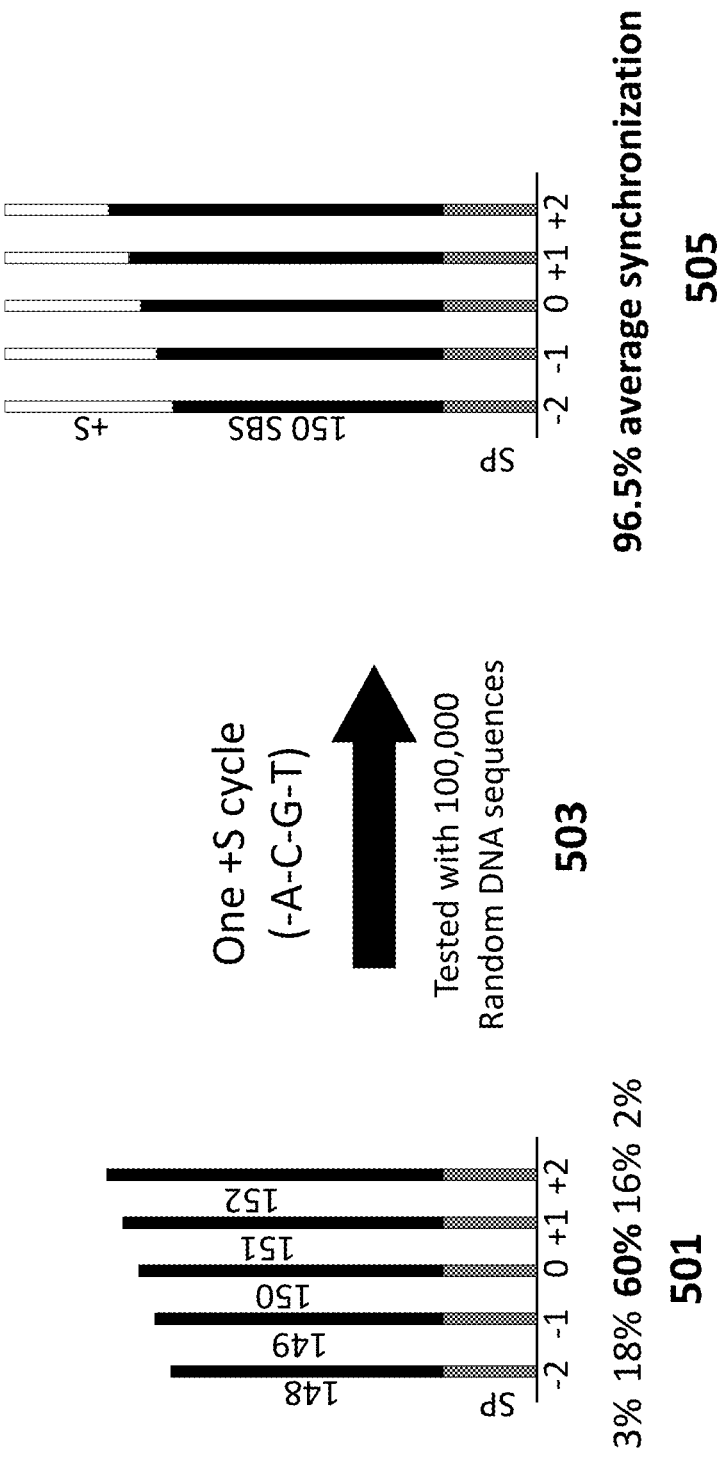
FIG. 5 depicts an example of utilizing multiple synchronization cycles to resynchronize sequencing strands in a cluster.

In some aspects, the methods provided herein may result in, after a synchronization cycle is performed, the resynchronization of up to 100% of the strands in a cluster. In some cases, the resynchronization may be 90%, 90.5%, 91%, 91.%, 92%, 92.5%, 93%, 93.5%, 94%, 94.5%, 95%, 95.5%, 96%, 96.5%, 97%, 97.5, 98%, 98.5%, 99%, 99.5%, 99.9% or 100% of the strands within a cluster. FIG. 5 depicts an example of four synchronization steps performed after 150 sequencing-by-synthesis (SBS) rounds (60% of the strands synchronized) 501. After performing four synchronization steps 503, on average, 96.5% of the strands were resynchronized 505.

The number of synchronization steps performed may further increase the effectiveness of the methods. For example, in FIG. 6, it was determined that after 16 synchronization steps, on average, 97.3% of the strands in a cluster were resynchronized.

In some cases, a large number of target nucleic acids (e.g. at least 10, 100, 1,000, 10,000, 100,000, or 1,000,000) are sequenced simultaneously. These target nucleic acids can be DNA, RNA or modified nucleic acids. While they can be sequenced as single molecules, they can also be sequenced as clones or clusters. Each of the clones or clusters (e.g. on beads) are derived from a single nucleic acid molecule. Methods for sequencing a large number of target nucleic acids in single molecule or clonal molecular clusters or beads are well known in the art. For simplicity of illustration, some examples may be described using singular terms such as "a target nucleic acid" or "an extension primer," one of skill in the art would appreciate that many of the embodiments can be used to sequence many target nucleic acids simultaneously or sequentially and such sequencing may be performed on copies (more than 10, 100, 1,000, 100,000 copies) of the target nucleic acids.

Target or Target Nucleic Acid

In one aspect, the present invention provides a method for sequencing a target nucleic acid molecule or a collection of target nucleic acids. By "target nucleic acid molecule", "target molecule", "target polynucleotide", "target polynucleotide molecule" or grammatically equivalent thereof, as used herein it is meant a nucleic acid of interest. Target nucleic acid, for example, can be DNA or RNA or any synthetic structure that have similar properties of DNA or RNA. Sequencing, as used herein, refers to the determination of at least a single base, at least 2 consecutive bases, at least 10 consecutive bases or at least 25 consecutive bases in a target nucleic acid. Sequencing accuracy can be at least 65%, 75%, 85, 95%, 99%, 99.9% and 99.99% overall or per base. Sequencing can be performed directly on a target nucleic acid or on a nucleic acid derived from target nucleic acids. In some applications, a large number of target nucleic acids, such as at least 1,000, 10,000, 100,000 or 1,000,000 target nucleic acids are simultaneously sequenced.

In some cases, a target nucleic acid is genomic DNA derived from the genetic material in the chromosomes of a particular organism and/or in nonchromosomal genetic materials such as mitochondrial DNA. A genomic clone library is a collection of clones made from a set of randomly generated overlapping DNA fragments representing the entire genome of an organism. A genomic library is a collection of at least 2%, 5%, 10%, 30%, 50%, 70%, 80%, or 90% of the sequence or sequences in the genomic DNA of an organism.

Target nucleic acids include naturally occurring or genetically altered or synthetically prepared nucleic acids (such as genomic DNA from a mammalian disease model). Target nucleic acids can be obtained from virtually any source and can be prepared using methods known in the art. For example, target nucleic acids can be directly isolated without amplification using methods known in the art, including without limitation extracting a fragment of genomic DNA from an organism (e.g. a cell or bacteria) to obtain target nucleic acids. In another example, target nucleic acids can also be isolated by amplification using methods known in the art, including without limitation polymerase chain reaction (PCR), whole genome amplification (WGA), multiple displacement amplification (MDA), rolling circle amplification (RCA), rolling circle amplification (RCR) and other amplification methodologies. Target nucleic acids may also be obtained through cloning, including cloning into vehicles such as plasmids, yeast, and bacterial artificial chromosomes. "Amplification" refers to any process by which the copy number of a target sequence is increased. Amplification can be performed by any means known in the art. Methods for primer-directed amplification of target polynucleotides are known in the art, and include without limitation, methods based on the polymerase chain reaction (PCR). Examples of PCR techniques that can be used include, but are not limited to, quantitative PCR, quantitative fluorescent PCR (QF-PCR), multiplex fluorescent PCR (MF-PCR), real time PCR (RTPCR), single cell PCR, restriction fragment length polymorphism PCR (PCR-RFLP), PCK-RFLPIRT-PCR-IRFLP, hot start PCR, nested PCR, in situ polony PCR, in situ rolling circle amplification (RCA), bridge PCR, picotiter PCR and emulsion PCR. Conditions favorable to the amplification of target sequences by PCR are known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are well known in the art and include adjustments to the type or amount of elements in the amplification reaction and/or to the conditions of a given step in the process, such as temperature at a particular step, duration of a particular step, and/or number of cycles. In some cases, an amplification reaction comprises at least 5, 10, 15, 20, 25, 30, 35, 50, or more cycles. In some cases, an amplification reaction comprises no more than 5, 10, 15, 20, 25, 35, 50, or more cycles. Cycles can contain any number of steps, such as 1, 2, 3, 4, 5, 6, 7, 8, 9, 10 or more steps. Steps can comprise any temperature or gradient of temperatures, suitable for achieving the purpose of the given step, including but not limited to, 3' end extension (e.g. adapter fill-in), primer annealing, primer extension, and strand denaturation. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, or more seconds, including indefinitely until manually interrupted. Cycles of any number comprising different steps can be combined in any order. In some cases, different cycles comprising different steps are combined such that the total number of cycles in the combination is about, less that about, or more than about 5, 10, 15, 20, 25, 30, 35, 50, or more cycles. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938. In some cases, the amplification is performed inside a cell.

In any of the examples, amplification may occur on a support, such as a bead or a surface. In any of the examples herein, targets may be amplified from an extract of a single cell.

Target nucleic acids may also have an exogenous sequence, such as a universal primer sequence or barcode sequence introduced during, for example, library preparation via a ligation or amplification process. The term "sequencing template" used herein may refer to the target nucleic acid itself or to a nucleotide sequence that is identical or substantially similar to the nucleotide sequence of a fragment of a target nucleic acid or the complement of a target nucleic acid. In some cases, the target nucleic acid molecule comprises ribonucleic acid (RNA).

In some cases, the target polynucleotide is genomic DNA or a portion of the genomic DNA. While some examples are for sequencing a whole genome, such as at more than 50% coverage, these examples are also suitable for sequencing a targeted region such as genomic regions relating to drug metabolism. In one example, the target polynucleotide is human genomic DNA.

Target nucleic acid, as used herein, can also refer to nucleic acid structures for sequencing. Such structures typically comprise adaptor sequences on one or both ends of target nucleic acid sequences. For example, a sequence derived from the genomic DNA of sample or derived from a RNA molecule of a sample, may be ligated with amplification and/or sequencing adaptor(s). Library construction methods are well known in the art. Nucleic acid sequencing libraries may be amplified in clonal fashion on substrates using bridge amplifications, emulsion PCR amplifications, rolling cycle amplifications or other amplification methods. Such processes may be performed manually or using automation equipment such as the cBot (Illumina, Inc.) or OneTouch™ (Ion Torrent).

"Nucleic acid" or "oligonucleotide" or "polynucleotide" or grammatical equivalents typically refer to at least two nucleotides covalently linked together. A nucleic acid of the present invention will generally contain phosphodiester bonds, although in some cases, as outlined below (for example in the construction of primers and probes such as label probes), nucleic acid analogs are included that may have alternate backbones, comprising, for example, phosphoramide (see e.g. Beaucage et al., Tetrahedron 49(10): 1925 (1993); Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 (1986)), phosphorothioate (Mag et al., Nucleic Acids Res. 19:1437 (1991); and U.S. Pat. No. 5,644,048), phosphorodithioate (see e.g. Briu et al., J. Am. Chem. Soc. 111:2321 (1989)), O-methylphophoroamidite linkages (see e.g. Eckstein, Oligonucleotides and Analogues: A Practical Approach, Oxford University Press), and peptide nucleic acid (also referred to herein as "PNA") backbones and linkages (see e.g. Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996)).

Other analog nucleic acids include those with bicyclic structures including locked nucleic acids, also referred to herein as "LNA", (see e.g. Koshkin et al., J. Am. Chem. Soc. 120.13252 3 (1998)); positive backbones (Denpcy et al., Proc. Natl. Acad. Sci. USA 92:6097 (1995)); non-ionic backbones (see e.g. U.S. Pat. Nos. 5,386,023, 5,637,684, 5,602,240, 5,216,141 and 4,469,863; Kiedrowshi et al., Angew. Chem. Intl. Ed. English 30:423 (1991)); Letsinger et al., J. Am. Chem. Soc. 110:4470 (1988); Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook.

Nucleic acids containing one or more carbocyclic sugars are also included within the definition of nucleic acids (see e.g. Jenkins et al., Chem. Soc. Rev. (1995) pp 169 176). Several nucleic acid analogs are described in Rawls, C & E News Jun. 2, 1997 page 35.

The target nucleic acids may be single stranded or double stranded, as specified, or contain portions of both double stranded or single stranded sequence. Depending on the application, the nucleic acids may be DNA (including genomic and cDNA), RNA (including mRNA and rRNA) or a hybrid, where the nucleic acid contains any combination of deoxyribo- and ribo-nucleotides, and any combination of bases, including uracil, adenine, thymine, cytosine, guanine, inosine, xathanine, hypoxathanine, isocytosine, isoguanine, etc.

In some cases, the methods of the present invention comprise capture of a target polynucleotide. The target polynucleotide may be from a known region of the genome. In some cases, oligonucleotide probes can be immobilized on beads and these oligonucleotide beads which are inexpensive and reusable can be used to capture the target genomic polynucleotide. In other cases, microarrays are used to capture target polynucleotide.

In some cases, the target polynucleotide may be fragmented to a suitable length or plurality of suitable lengths, such as approximately between 100-200, 200-300, 300-500, 500-1000, 1000-2000 or more bases in length.

Naturally-existing targets can be assayed directly in cell lysates, in nucleic acid extracts, or after partial purification of fractions of nucleic acids so that they are enriched in targets of interest. In one example, the target polynucleotide is human genomic DNA. The polynucleotide target to be detected can be unmodified or modified. Useful modifications include, without limitation, radioactive and fluorescent labels as well as anchor ligands such as biotin or digoxigenin. The modification(s) can be placed internally or at either the 5' or 3' end of the targets. Target modification can be carried out post-synthetically, either by chemical or enzymatic reaction such as ligation or polymerase-assisted extension. Alternatively, the internal labels and anchor ligands can be incorporated into an amplified target or its complement directly during enzymatic polymerization reactions using small amounts of modified NTPs as substrates.

The target polynucleotide can be isolated from a subject. The subject is not limited to a human being but may also be other organisms including but not limited to mammals, plants, bacteria, virus or fungi. In one example, the target polynucleotide is genomic DNA extracted from a human.

The input nucleic acid can be DNA, or complex DNA, for example genomic DNA. The input DNA may also be cDNA. The cDNA can be generated from RNA, e.g., mRNA. The input DNA can be of a specific species, for example, human, rat, mouse, other animals, plants, bacteria, algae, viruses, and the like. The input nucleic acid also can be from a mixture of genomes of different species such as host-pathogen, bacterial populations and the like. The input DNA can be cDNA made from a mixture of genomes of different species. Alternatively, the input nucleic acid can be from a synthetic source. The input DNA can be mitochondrial DNA. The input DNA can be cell-free DNA. The cell-free DNA can be obtained from, e.g., a serum or plasma sample. The input DNA can comprise one or more chromosomes. For example, if the input DNA is from a human, the DNA can comprise one or more of chromosome 1, 2, 3, 4, 5, 6, 7, 8, 9, 10, 11, 12, 13, 14, 15, 16, 17, 18, 19, 20, 21, 22, X, or Y. The DNA can be from a linear or circular genome. The DNA can be plasmid DNA, cosmid DNA, bacterial artificial chromosome (BAC), or yeast artificial chromosome (YAC). The input DNA can be from more than one individual or organism. The input DNA can be double stranded or single stranded. The input DNA can be part of chromatin. The input DNA can be associated with histones. The methods described herein can be applied to high molecular weight DNA, such as is isolated from tissues or cell culture, for example, as well as highly degraded DNA, such as cell-free DNA from blood and urine and/or DNA extracted from formalin-fixed, paraffin-embedded tissues, for example.

The different samples from which the target polynucleotides are derived can comprise multiple samples from the same individual, samples from different individuals, or combinations thereof. In some cases, a sample comprises a plurality of polynucleotides from a single individual. In some cases, a sample comprises a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. Sample polynucleotides can be isolated from a subject, such as a cell sample, tissue sample, or organ sample derived therefrom, including, for example, cultured cell lines, biopsy, blood sample, or fluid sample containing a cell. The subject may be an animal, including but not limited to, an animal such as a cow, a pig, a mouse, a rat, a chicken, a cat, a dog, etc., and is usually a mammal, such as a human. Samples can also be artificially derived, such as by chemical synthesis. In some cases, the samples comprise DNA. In some cases, the samples comprise genomic DNA. In some cases, the samples comprise mitochondrial DNA, chloroplast DNA, plasmid DNA, bacterial artificial chromosomes, yeast artificial chromosomes, oligonucleotide tags, or combinations thereof. In some cases, the samples comprise DNA generated by primer extension reactions using any suitable combination of primers and a DNA polymerase, including but not limited to polymerase chain reaction (PCR), reverse transcription, and combinations thereof. Where the template for the primer extension reaction is RNA, the product of reverse transcription is referred to as complementary DNA (cDNA). Primers useful in primer extension reactions can comprise sequences specific to one or more targets, random sequences, partially random sequences, and combinations thereof. Reaction conditions suitable for primer extension reactions are known in the art. In general, sample polynucleotides comprise any polynucleotide present in a sample, which may or may not include target polynucleotides.

Sequencing

The methods provided herein are amenable to sequencing technologies and platforms that use sequencing-by-synthesis methods. Overall such methods involve sequencing a target nucleic acid molecule having a plurality of bases by the temporal addition of bases via a polymerization reaction that is measured on a molecule of nucleic acid, i e., the activity of a nucleic acid polymerizing enzyme on the template nucleic acid molecule to be sequenced is followed in real time. Sequence can then be deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishable type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The rounds of providing labeled nucleotide analogs, polymerizing the growing nucleic acid strand, and identifying the added nucleotide analog are repeated so that the nucleic acid strand is further extended and the sequence of the target nucleic acid is determined. Non-limiting examples of sequencing platforms for which the methods described can be utilized include: SBS platforms from Illumina including MiSeq series, HiSeq series, NextSeq series and HiSeqX series; IonTorrent (Life Technologies, Inc.); and 454 Pyrosquencing (454 Life Sciences). Essentially any SBS platform that uses template amplification can be used to perform the methods of the disclosure.

In one case, sequencing can be conducted with labeled nucleotides such as dNTPs with labels. Bases may be detected by extending the incremental fragments via contacting the hybridization complexes sequentially with one of labeled dATP, dCTP, dGTP and dTTP, in the presence of a polymerase, and detecting the incorporation of the labeled dATP, dCTP, dGTP and dTTP to obtain a sequence read from each reaction.

In one example, a mixture of labeled dATP, dCTP, dGTP and dTTP are used. Generally, due to general low incorporation efficiency of the modified dNTPs, such as labeled dNTPs, only the first few bases are extended to generate strong signal. The possibility of "run-on" extension is rather low and the signal generated by such "run-on" extension can be filtered out as noise using methods provided herein or known in the art. In one example, a mixture of labeled ddATP, ddCTP, ddGTP and ddTTP are used, and no "run-on" extension is permitted. In one example, only one round of interrogation that covers all four possible bases is carried for each incremental fragment. For example, sequential addition with one labeled dNTP in each round of interrogation provides possible addition of one detectable base at a time (i.e. on each substrate). This generally results in short read (such as one base or a few bases) that could be assembled for each round. In another example, a longer read is generated with more than one round of interrogation.

In another example, a mixture of labeled ddATP, ddCTP, ddGTP, ddTTP and small amount (<10% (e.g. 5, 6, 7, 8, or 9%) or <20% (e.g., 10, 11, 12, 13, 14, 15, 16, 17, 18, or 19%) of native dATP, dCTP, dGTP, and dTTP are added.

In some cases, the labeled nucleotides are reversible terminators. Multiple bases can be detected by the signal strength or in the case of reversible terminator, base addition detection. Nucleotide reversible terminators are nucleotide analogues, which are modified with a reversible chemical moiety capping the 3'-OH group to temporarily terminate the polymerase reaction. In this way, generally only one nucleotide is incorporated into the growing DNA strand even in homopolymeric regions. For example, the 3' end can be capped with an amino-2-hydroxypropyl group. An allyl or a 2-nitrobenzyl group can also be used as the reversible moiety to cap the 3'-OH of the four nucleotides. Examples of reversible terminators include but are not limited to 3'-O-modified nucleotides such as 3'-O-allyl-dNTPs and 3'-O-(2-nitrobenzyl)-dNTPs.

In some cases, after detection of the cleavage site present on the solution probe, the 3'-OH of the primer extension products is regenerated through different deprotection methods. The capping moiety on the 3'-OH of the DNA extension product can be efficiently removed after detection of a cleavage site by a chemical method, enzymatic reaction or photolysis, i.e. the cap will be cleaved from the cleavage site. To sequence DNA, in some cases, templates containing homopolymeric regions are immobilized on Sepharose beads, and then extension—signal detection—deprotection cycles are conducted by using the nucleotide reversible terminators on the DNA beads to unambiguously decipher the sequence of DNA templates. In some cases, this reversible-terminator-sequencing approach is used in the subject methods to accurately determine DNA sequences. (The cap may be referred to herein as a "protective group").

In some cases, polynucleotides of the invention can be labeled. In some cases, a molecule or compound has at least one detectable label (e.g., isotope or chemical compound) attached to enable the detection of the compound. In general, labels of use in the present invention include without limitation isotopic labels, which may be radioactive or heavy isotopes, magnetic labels, electrical labels, thermal labels, colored and luminescent dyes, enzymes and magnetic particles as well. Labels can also include metal nanoparticles, such as a heavy element or large atomic number element, which provide high contrast in electron microscopy. Dyes of use in the invention may be chromophores, phosphors or fluorescent dyes, which due to their strong signals provide a good signal-to-noise ratio for decoding.

In some cases, labels may include the use of fluorescent labels. Suitable dyes for use in the present invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue, Texas Red, and others described in the 11th Edition of the Molecular Probes Handbook by Richard P. Haugland, hereby expressly incorporated by reference in its entirety. Commercially available fluorescent nucleotide analogues readily incorporated into the labeling oligonucleotides include, for example, Cy3-dCTP, Cy3-dUTP, Cy5-dCTP, Cy5-dUTP (GE Healthcare), fluorescein-12-dUTP, tetramethylrhodamine-6-dUTP, Texas Red®-5-dUTP, Cascade Blue®-7-dUTP, BODIPY® FL-14-dUTP, BODIPY®R-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-1 4-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-1 4-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, and Alexa Fluor® 546-1 4-UTP (Invitrogen). Other fluorophores available for post-synthetic attachment include, inter alia, Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Invitrogen), and Cy2, Cy3.5, Cy5.5, and Cy7 (GE Healthcare).

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, 7,689,022 and in WO99/47964, each of which also is hereby incorporated by reference in its entirety for all purposes. Fluorescence imaging and software programs or algorithms for DNA sequence analysis and read interpretation are known to one of ordinary skill in the art and are disclosed in Harris T D, et al. "Single-Molecule DNA Sequencing of a Viral Genome" *Science* 4 Apr. 2008: Vol. 320. no. 5872, pp. 106-109, which is herein incorporated by reference in its entirety. In some cases, Phred software is used for DNA sequence analysis. Phred reads DNA sequencer trace data, calls bases, assigns quality values to the bases, and writes the base calls and quality values to output files. Phred is a widely-used program for base calling DNA sequencing trace files. Phred can read trace data from SCF files and ABI model 373 and 377 DNA sequencer chromat files, automatically detecting the file format. After calling bases, Phred writes the sequences to files in either FASTA format, the format suitable for XBAP, PHD format, or the SCF format. Quality values for the bases are written to FASTA format files or PHD files, which can be used by the phrap sequence assembly program in order to increase the accuracy of the assembled sequence. The quality value is a log-transformed error probability, specifically $Q=-10 \log_{10}(P_e)$ where $Q$ and $P_e$ are respectively the quality value and error probability of a particular base call. The Phred quality values have been thoroughly tested for both accuracy and power to discriminate between correct and incorrect base-calls. Phred can use the quality values to perform sequence trimming.

DNA polymerase based sequencing reactions generally possess efficiency problems. Native nucleotides can be incorporated at a relatively high efficiency, compared to reduced efficiency incorporation of non-native nucleotides, such as labeled nucleotides or reversible terminators. Thus, in a growing strand of a nucleotide extension reaction, the likelihood of elongation drops as a function of the extended length. Thus, even slight differences in single nucleotide incorporation efficiency can lead to significant differences, as the reaction proceeds. The reduced incorporation efficiency accounts for increased error rates and hence decreased sequence information quality along growing strands. The resulting sequence information consists of relatively short sequence reads that have been terminated due to unacceptably low correct sequence signal. The present invention provides methods and compositions to overcome these problems in sequencing reactions.

Immobilized Target

In some cases, a nucleic acid target is attached to a substrate or immobilized on a substrate. The substrate can be a bead, flat substrate, flow cell or other suitable surfaces. In some cases, the substrate comprises glass.

In some cases, a target nucleic acid is attached or immobilized to a substrate via a capture probe. A capture probe is an oligonucleotide that is attached to the surface of a substrate and is capable to bind to a sequencing template. Capture probes can be of various lengths, such as from 18 bases to 100 bases, such as 20 bases to 50 bases.

In some cases, the capture probe has a sequence that is complementary to the sequencing template. For example, if the present method is used to sequence a genome with at least partial sequence known already, capture probes can be designed to complement to the known sequences. In some cases, the capture probes are complementary to a "barcode" or "identifier" sequence added to the sequencing templates via, e.g., specific ligation, as a part of the primer for PCR reaction. In such reactions, a sequencing template-specific primer and a primer comprising a unique barcode are used for the amplification, thus all the target molecules with the same sequences have the same barcode attached.

The capture probe can be attached to the substrate at either the 5' end or the 3' end. In some cases, the capture probe is attached to the substrate at the 5' end, and the 3' end of the capture probe can be extended by the incorporation of nucleotides as described herein to generate incremental extension fragments which can in turn be sequenced by further incorporation of labeled nucleotides. In other cases, the capture probe is attached to the substrate at the 3' end, and the 5' end of the capture probe cannot be extended by the incorporation of nucleotides. A second probe (or sequencing primer) hybridizes to the sequencing template and its 3' end is extended by the incorporation of nucleotides as described herein to generate an incremental extension fragment which can in turn be sequenced by further incorporation of labeled nucleotides. In this case, the extension is towards the direction of the capture probe. In general, the sequencing primer hybridizes to a linker introduced to the end of the sequencing template when generated, either directly from a genomic DNA or from a parent target molecule. Thus a seed/sequencing primer that is a "universal primer" can be used to sequence different target molecules. In some cases, sequencing primers specific to the target molecule are used.

In some cases, the capture probe is immobilized on a solid support before binding to the sequencing template. In some cases, the 5' end of a capture probe is attached to a solid surface or substrate. A capture probe can be immobilized by various methods known in the art including, without limitation, covalent cross-linking to a surface (e.g., photochemically or chemically), non-covalent attachment to the surface through the interaction of an anchor ligand with a corresponding receptor protein (e.g. biotin-streptavidin or digoxigenin-anti-digoxigenin antibody), or through hybridization to an anchor nucleic acid or nucleic acid analog. The anchor nucleic acid or nucleic acid analog have sufficient complementarity to the sequencing template (i.e., the formed duplex has sufficiently high $T_m$) that the anchor-sequencing template-probe complex will survive stringent washing to remove unbound targets and probes, but they do not overlap with the target site that is complementary to the probe antisense sequence.

In some cases, a capture template or target nucleic acid is used as a template for bridge amplification. In such cases, two or more different immobilized probes are used. In some cases, single molecule templates are used to generate clusters of nucleic acids on a substrate by bridge amplification. In some cases, each of the clusters of nucleic acids contains substantially the same (>95%) type of nucleic acids because they are derived from a single template nucleic acid. These clusters are typically referred to as single molecule clusters.

Such substrates with single molecular clusters can be produced using, for example, the method described in Bently et al., Accurate whole human genome sequencing using reversible terminator chemistry, Nature 456, 53-59 (2008), incorporated herein by reference, or using commercially available kit and instrument from, for example, Illumina, Inc. (San Diego, Calif.)

An immobilized or attached target nucleic acid can then be hybridized with a primer (or multiple primers). Polymerase in its suitable buffer is then added to make contact with the immobilized or attached template or target nucleic acid. The primer can be used directly as a sequencing primer.

Sequencing Systems

Figure 8:
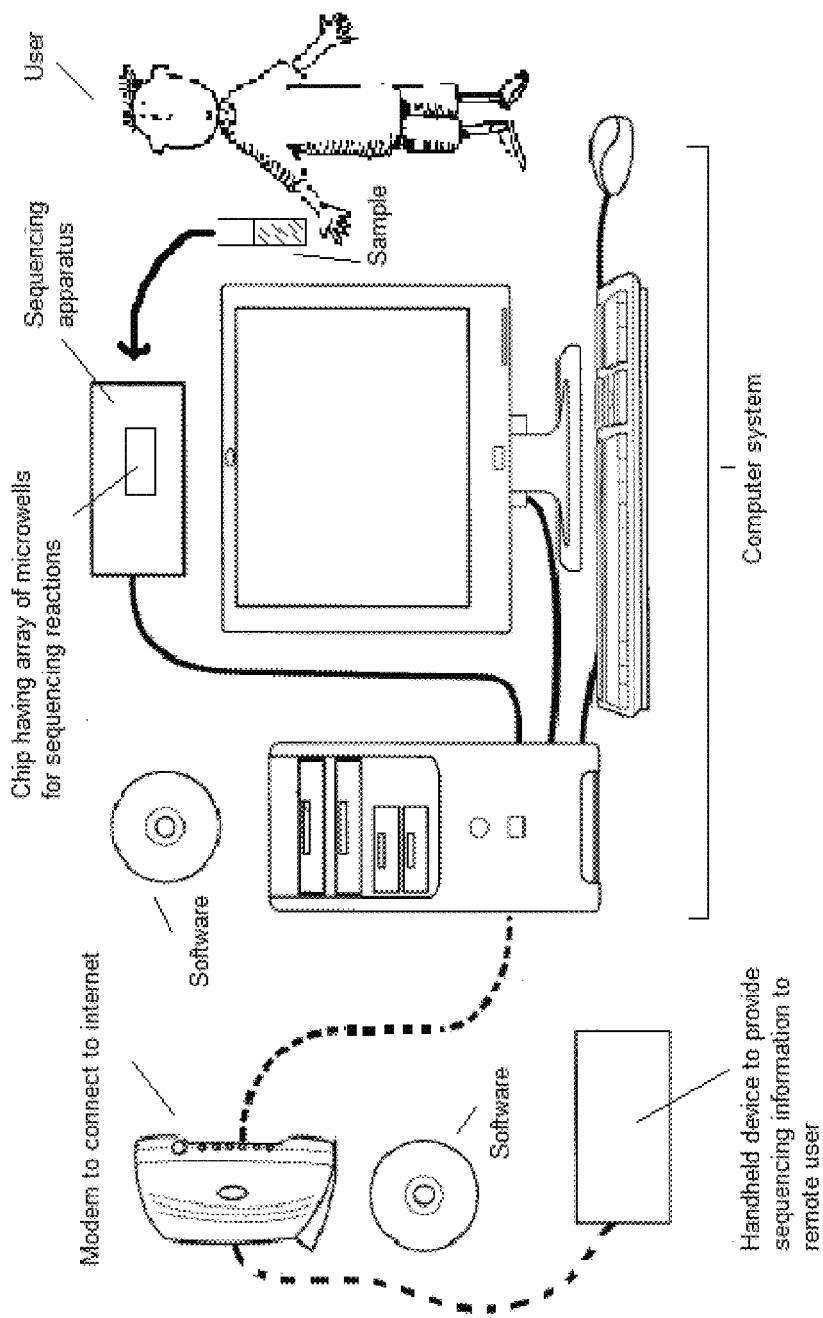
FIG. 8 depicts an example of a computer system amenable for use with the methods provided herein.

In another aspect, the present invention provides a system for sequencing. In some cases, one or more methods of sequencing disclosed herein are performed by a system, such as an automated sequencing system instrument controlled by a user (e.g., as schematically depicted in FIG. 8). In some cases, the user controls a computer which may operate various instrumentation, liquid handling equipment or analysis steps of the invention. In some cases, a computer controlled collection, handling, or analysis system is used to control, activate, initiate, continue or terminate any step or process of the methods as herein described. In some cases, a computer device is used to control, activate, initiate, continue or terminate the handling and/or movement of fluids or reagents into and through the system or device as herein described, the handling or movement of one or more reagents to one or more chambers or plurality of chambers in one or more cartridges, the obtaining or analysis of data, etc. In some cases, chips of the sequencing reaction are placed in one or more chambers/flow cells or plurality of chambers/flow cells in one or more cartridges. The chips may comprise substrates which provide sites for the sequencing reactions.

In some cases, the computer is any type of computer platform such as a workstation, a personal computer, a server, or any other present or future computer. The computer typically includes known components such as a processor, an operating system, system memory, memory storage devices, and input-output controllers, input-output devices, and display devices. Such display devices include display devices that provides visual information, this information typically may be logically and/or physically organized as an array of pixels. In some cases, a graphical user interface (GUI) controller is included that comprises any of a variety of known or future software programs for providing graphical input and output interfaces. In some cases, GUI's provide one or more graphical representations to the user, and are enabled to process the user inputs via GUI's using means of selection or input known to those of ordinary skill in the related art.

It will be understood by those of ordinary skill in the relevant art that there are many possible configurations of the components of a computer and that some components that may typically be included in a computer are not described, such as cache memory, a data backup unit, and many other devices. In the present example each execution core may perform as an independent processor that enables parallel execution of multiple threads.

In some cases, the processor executes operating system, which is, for example, a WINDOWS™ type operating system (such as WINDOWS™ XP) from the Microsoft Corporation; the Mac OS X operating system from Apple Computer Corp. (such as 7.5 Mac OS X v10.4 "Tiger" or 7.6 Mac OS X v10.5 "Leopard" operating systems); a UNIX™ or Linux-type operating system available from many vendors or what is referred to as an open source; or a combination thereof. The operating system interfaces with firmware and hardware in a well-known manner, and facilitates processor in coordinating and executing the functions of various computer programs that may be written in a variety of programming languages. The operating system, typically in cooperation with the processor, coordinates and executes functions of the other components of computer. The operating system also provides scheduling, input-output control, file and data management, memory management, and communication control and related services, all in accordance with known techniques.

In some cases, the system memory is of a variety of known or future memory storage devices. Examples include any commonly available random access memory (RAM), magnetic medium such as a resident hard disk or tape, an optical medium such as a read and write compact disc, or other memory storage device. Memory storage devices may be any of a variety of known or future devices, including a compact disk drive, a tape drive, a removable hard disk drive, USB or flash drive, or a diskette drive. Such types of memory storage devices typically read from, and/or write to, a program storage medium (not shown) such as, respectively, a compact disk, magnetic tape, removable hard disk, USB or flash drive, or floppy diskette.

In some cases, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

In some cases, input-output controllers include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers of input-output controllers could include controllers for any of a variety of known display devices for presenting information to a user, whether a human or a machine, whether local or remote. In some cases, the functional elements of computer communicate with each other via system bus. Some of these communications may be accomplished in alternative examples using network or other types of remote communications.

In some cases, applications communicate with, and receive instruction or information from, or control one or more elements or processes of one or more servers, one or more workstations, and/or one or more instruments. In some cases, a server or computer with an implementation of applications stored thereon are located locally or remotely and communicate with one or more additional servers and/or one or more other computers/workstations or instruments. In some cases, applications are capable of data encryption/decryption functionality. For example, it may be desirable to encrypt data, files, information associated with GUI's or other information that may be transferred over network to one or more remote computers or servers for data security and confidentiality purposes.

In some cases, applications include instrument control features, where the control functions of individual types or specific instruments such as a temperature controlling device, imaging device, or fluid handling system are organized as plug-in type modules to the applications. In some cases, the instrument control features include the control of one or more elements of one or more instruments that, for instance, include elements of a fluid processing instrument, temperature controlling device, or imaging device. In some cases, the instrument control features are capable of receiving information from the one or more instruments that include experiment or instrument status, process steps, or other relevant information. In some cases, the instrument control features are under the control of an element of the interface of the applications. In some cases, a user inputs desired control commands and/or receive the instrument control information via one of GUI's.

In some cases, the automated sequencing system is controlled by a first user, conducts sequencing methods described herein, analyzes the raw data as described herein, assembles sequence reads as described herein, and then send the sequencing information to a remote second user at a location different from that of the first user.

Processing of Data and Data Analysis

In some cases, identifying target polynucleotide sequence and integrating sequences to assemble genomic information is carried out with a computer. In some cases, the present invention encompasses a computer software or algorithm designed to analyze and assemble sequence information obtained via the methods of the present invention.

In terms of sequence read interpretation for the in situ arrays, reads at array features correspond to X-Y coordinates that map to the loci of interest. A "read" typically refers to an observed sequence derived from raw data, such as the order of detected signals corresponding to the cyclical addition of individual nucleotides. In some cases, the reads are checked against the expected reference genome sequence at the 10-bp loci for quality control. A reference sequence enables the use of short read length. Reads that have passed the quality control check are then combined to generate a consensus sequence at each locus. In one example, there are 10 unique probes per locus of interest minus any reads that have failed the quality control checks.

In terms of sequence read interpretation for the "lawn" approach, the reads are at random locations on a surface, e.g. a flow cell. In some cases, the reads are checked against the expected subset of reference genome sequence at the loci of interest for quality control. Reads that have passed the quality control check are mapped to the individual locus of interest. Reads corresponding to each locus are then combined to generate a consensus sequence. In some cases, there are more than 3,000 reads per 10-bp locus.

Assembly of Sequence Reads

In some cases, the present invention provides a method for obtaining the sequence information of the target molecules by assembling the sequence reads from each of the substrates. The sequence reads can be obtained by base extension of a series of polynucleotide with different lengths due to the different base extension of the same capture probe using the same target molecules, such as described above. As such, they represent continued fragments of the target molecule sequence and can be assembled to provide the continue sequence of the target molecule.

A computer program can be used to track the sequence reads obtained from the same capture probes on different substrates for the assembly.

In some cases, sequencing information originating from a single template is identified using a unique identifier of the template, such as the template location or a tag sequence. Overlapping sequence information can be stitched together to generate longer sequence information from a single template. In some cases, a template's complement is also sequenced. In some cases, sequence information is stitched together using sequence reads generated both from the template and its complement.

Performance

The methods, reagents and kits disclosed herein can improve the performance of nucleic acid sequencing reactions. In particular examples, the improvements in performance relate to an improvement in the synchronization of nucleic acid molecules during a sequencing reaction. An improvement in synchronization can relate to an improvement in the quality of sequencing reads.

Figure 9:
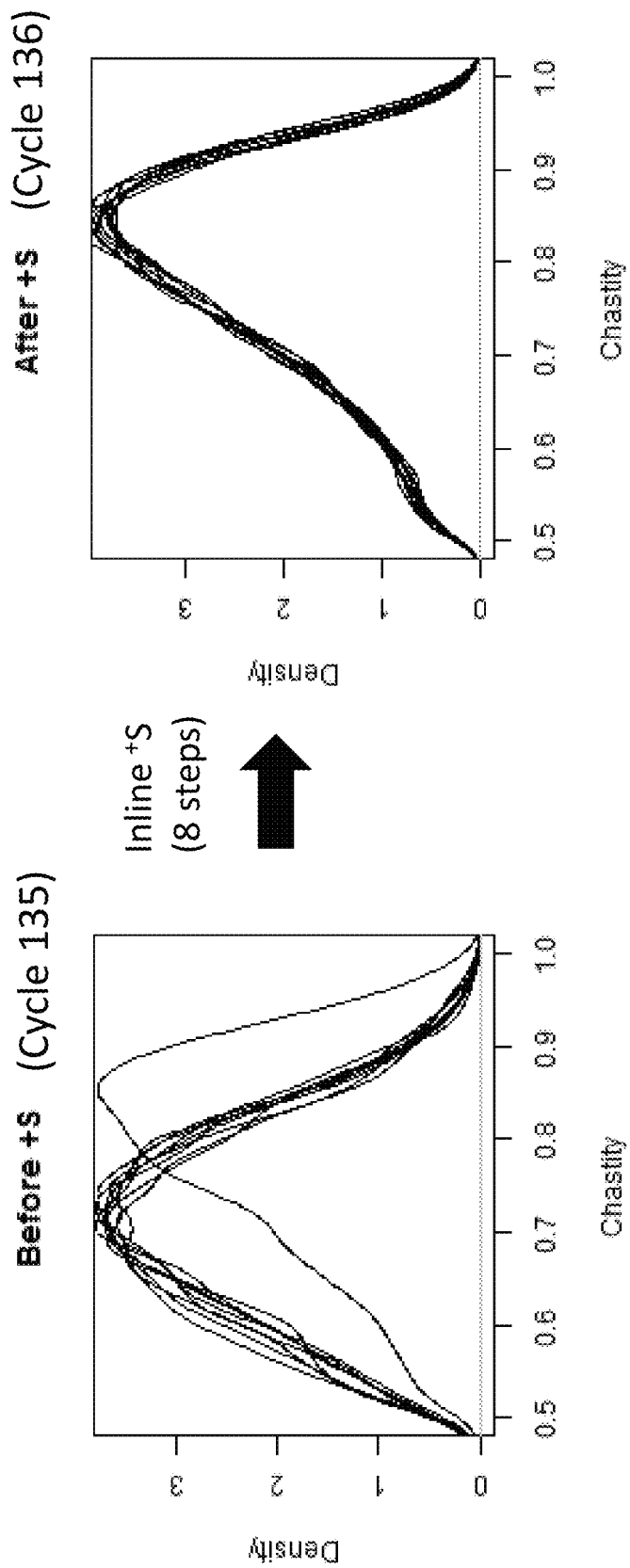
FIG. 9 depicts an increase in signal intensity utilizing the methods described herein.

The synchronization of nucleic acid molecules in a sequencing reaction can be measured by a chastity score. The chastity score is defined by the following formula: Chastity=$I_1/(I_1+I_2)$, wherein $I_1$ is the intensity of the strongest signal (i.e., the correct base incorporated) and $I_2$ is the intensity of the second strongest signal (i.e., an incorrect base incorporated). Thus, a chastity score is a measurement of the ratio of the amount of a correct base incorporated to a growing sequencing product to the sum of the amount of the correct base and the amount of the incorrect base incorporated to the growing sequencing product at a given time point. A chastity score is calculated for a cluster of nascent sequencing products and is a measurement of the extent of dephasing/prephasing occurring in that cluster. A chastity score can relate to a particular step of a sequencing cycle and can change over the duration of a sequencing reaction. For example, a chastity score can be calculated for a cluster of nascent sequencing products after a number of sequencing steps, for example, after 50, 100, 150, 200 or more sequencing steps. A chastity score will generally decrease as the sequencing product gets longer (i.e., more of the sequencing products get out-of-phase). The methods, reagents and kits provided herein can improve the chastity score of a cluster of sequencing products by improving the synchronization of the growing strands. In some cases, a chastity score, after performing the methods of the disclosure, will be 0.8, 0.85, 0.9, 0.95, 0.99, up to 1.0. In an example, a chastity score after performing the methods herein will be at least 0.85 or higher after performing a synchronization cycle, as described throughout the disclosure. Generally, a chastity score will improve after a synchronization cycle. A chastity score can be improved by 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 100% or greater than 100% after performing a synchronization cycle. In some cases, the chastity score is improved by at least 20%. In other cases, the chastity score is improved by at least 35%. In yet other cases, the chastity score is improved by at least 50%. FIG. 9 depicts an example of an improvement in chastity performing the methods provided herein. The strands prior to the synchronization cycle 901, on average, have a chastity score of ~0.7, whereas after the synchronization cycle (e.g., 8 synchronization steps), the average chastity score is ~0.85 903.

In some aspects, the methods and systems provided herein are amenable to improving the length of sequencing reads of a target nucleic acid sequence. In some cases, the length of sequencing reads of a target nucleic acid sequence is improved after performing a synchronization cycle. The length of sequencing reads may be improved relative to a sequencing method that does not utilize the synchronization methods described herein. In some cases, the length of sequencing reads is improved by generating longer sequencing reads with greater accuracy. In some cases, the methods and systems generate longer sequencing reads by about 300, 400, 500, 600, 700, 800, 900, 1000 or more base pairs. In some cases, a read error rate is decreased by about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100%.

In one aspect, a sequencing-by-synthesis (SBS) system is configured to produce sequencing reads greater than 300 base pairs and having a chastity score of at least 0.85 or greater. In another aspect, a method is provided for sequence determination wherein the method involves performing a sequencing-by-synthesis (SBS) reaction to generate sequencing reads greater than 300 base pairs and having a chastity score of at least 0.85 or greater. In another aspect, a method is provided of improving a chastity score of a sequencing reaction, wherein the chastity score is improved by at least 20%. In some cases, the method does not involve software.

Kits

Kits and reagents are further provided to perform the methods described herein. In some cases, a kit is provided for sequencing a target nucleic acid molecule. The kit may include one or more sequencing primers. The one or more sequencing primers can be hybridized to the target nucleic acid molecule. In some cases, the one or more sequencing primers may anneal to one or more adaptor, index, or barcode sequences present on the target nucleic acid. In other cases, the one or more sequencing primers may anneal directly to the target nucleic acid sequence. The kit may further include one or more labeled nucleotides. The one or more labeled nucleotides have been described above and can be utilized to perform the one or more sequencing cycles of the methods. In some cases, the one or more labeled nucleotides are fluorescently-labeled nucleotides. The kit may further include one or more sets of up to three different nucleotides selected from the group consisting of: dATP, dTTP, dCTP and dGTP. In some cases, dUTP may also be included in the set. In some cases, the sets of nucleotides are unlabeled nucleotides. The one or more sets of unlabeled nucleotides have been described above and can be utilized to perform the one or more synchronization steps of the methods. In some cases, the one or more sets of unlabeled nucleotides include native nucleotides. Kits can include one or more of the following sets of unlabeled nucleotides: dATP, dCTP and dGTP ("-T"); dATP, dTTP and dGTP ("-C"); dCTP, dGTP and dTTP ("-A"); and dATP, dCTP and dTTP (-"G"). Alternatively or additionally, kits can include sets of nucleotides that include a reversible terminator nucleotide and three unlabeled nucleotides (e.g., dATP, dCTP, dGTP and a reversible terminator dTTP).

Kits may further include one or more of the following: a polymerase (e.g., DNA polymerase), a pyrophosphatase, an apyrase, a buffer, or any additional reagent amenable to performing the methods described herein. The kit may further include instructions that describe the use of the reagents and how to perform the methods described above.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Figure 10:
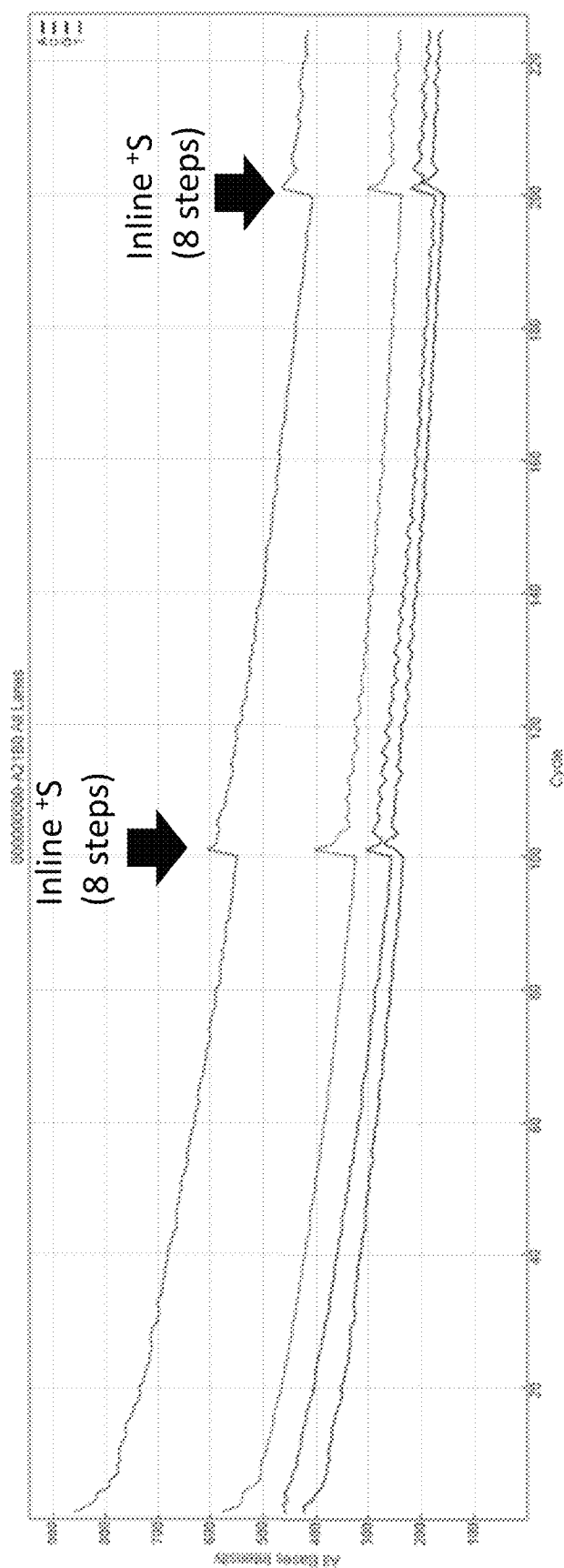
FIG. 10 depicts an increase in quality score utilizing the methods described herein.
Figure 11:
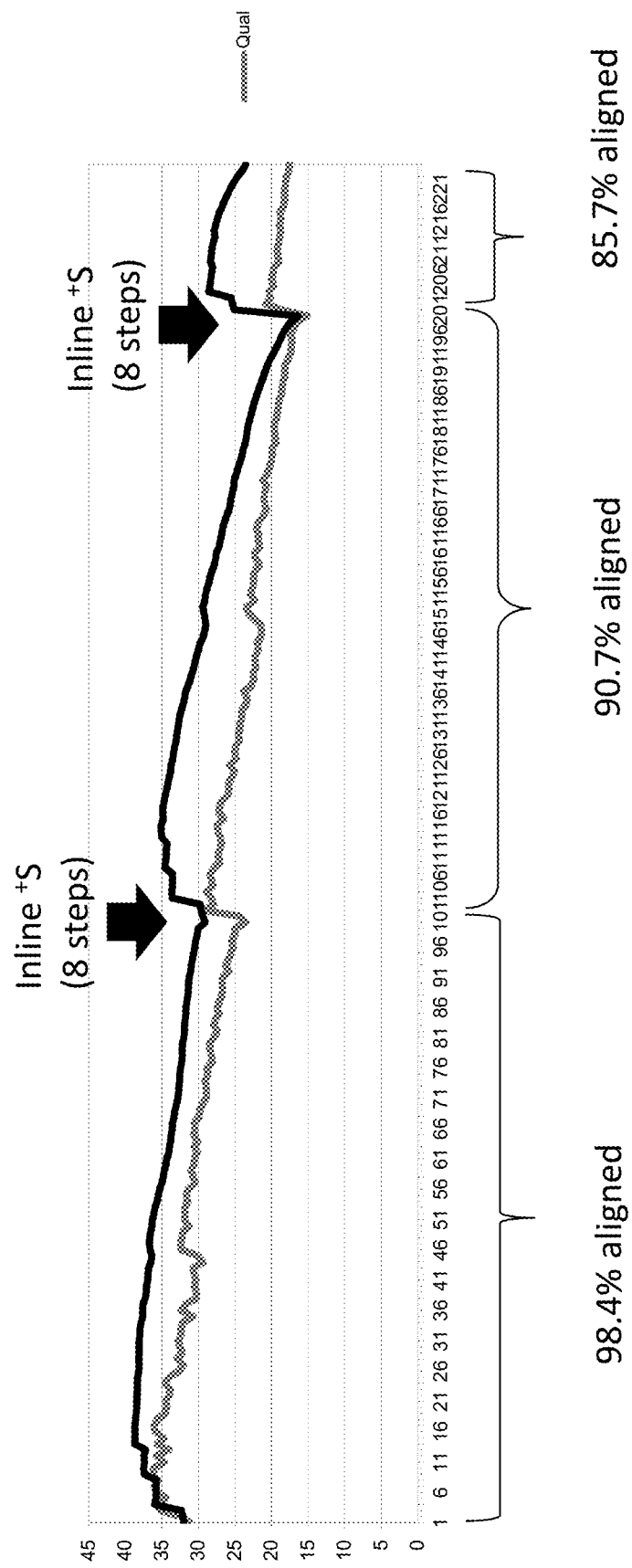
FIG. 11 depicts an increase in signal intensity utilizing the methods described herein.

Example 1—Inline +S Synchronization Resets Sequencing Strands after 100 Rounds of SBS Sequencing FIGS. 10 & 11 depict the results of a synchronization protocol. Briefly, sequencing-by-synthesis (SBS) reactions were performed on a MiSeq sequencing system (Illumina). After 100 rounds of SBS sequencing, the reactions were deblocked, the reactions were primed with apyrase followed by Mix0 at 37 C. Next, 8 inline +S synchronization steps were performed as follows: (-A, -C, -G, -T, -G, -C, -A, -T) to reset the sequencing strands. The synchronization protocol was followed by another 100 rounds of sequencing, followed by an additional 8 inline +S synchronization steps, and an additional 25 rounds of sequencing. FIG. 10 depicts the intensity signal measured for each nucleotide (y-axis) at each step (x-axis). The first inline +S protocol resulted in a 10.2% average intensity increase (A: 11%, C: 8.8%, G: 11.7%, and T: 9.4%), whereas the second inline +S protocol resulted in a 12.3% average intensity increase (A: 18.6%, C: 13.2%, G: 19.5%, and T: 10.8%). FIG. 11 depicts the quality score (y-axis) of the sequencing reads at each step (x-axis). FIG. 11 compares the reported Illumina quality score calculated by algorithm (black line) with the quality score calculated by aligning the data to a reference sequence (grey line).

Figure 12:
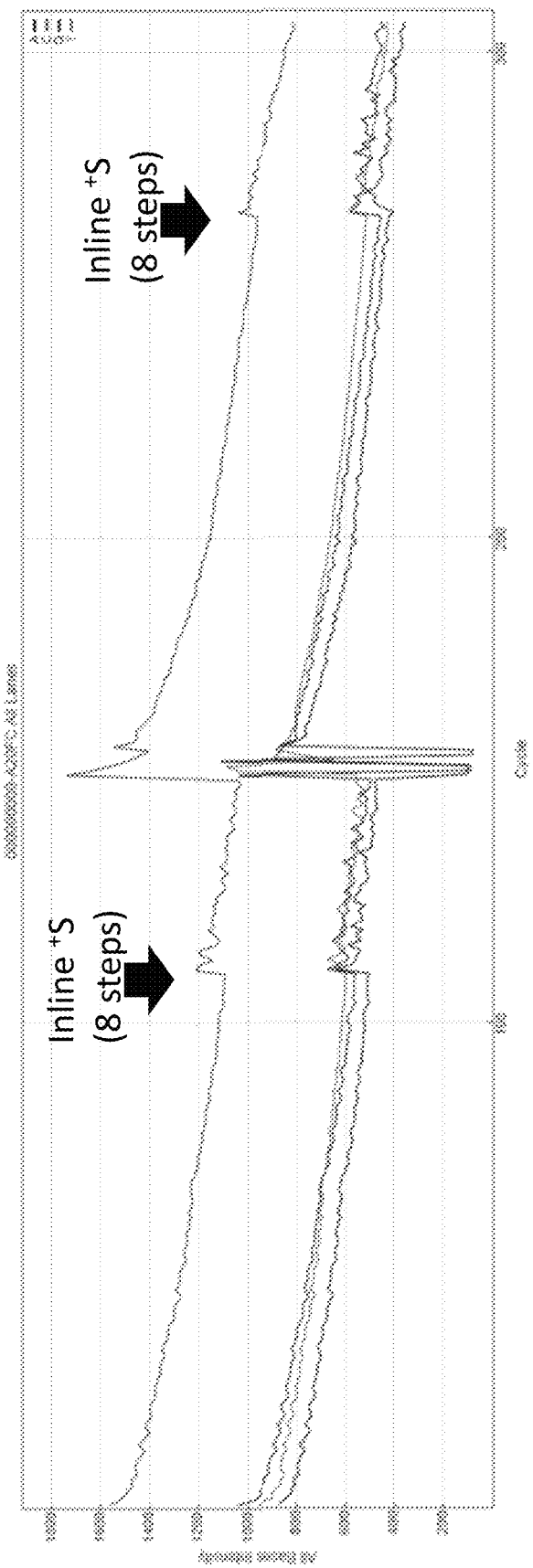
FIG. 12 depicts an increase in quality score utilizing the methods described herein.
Figure 13:
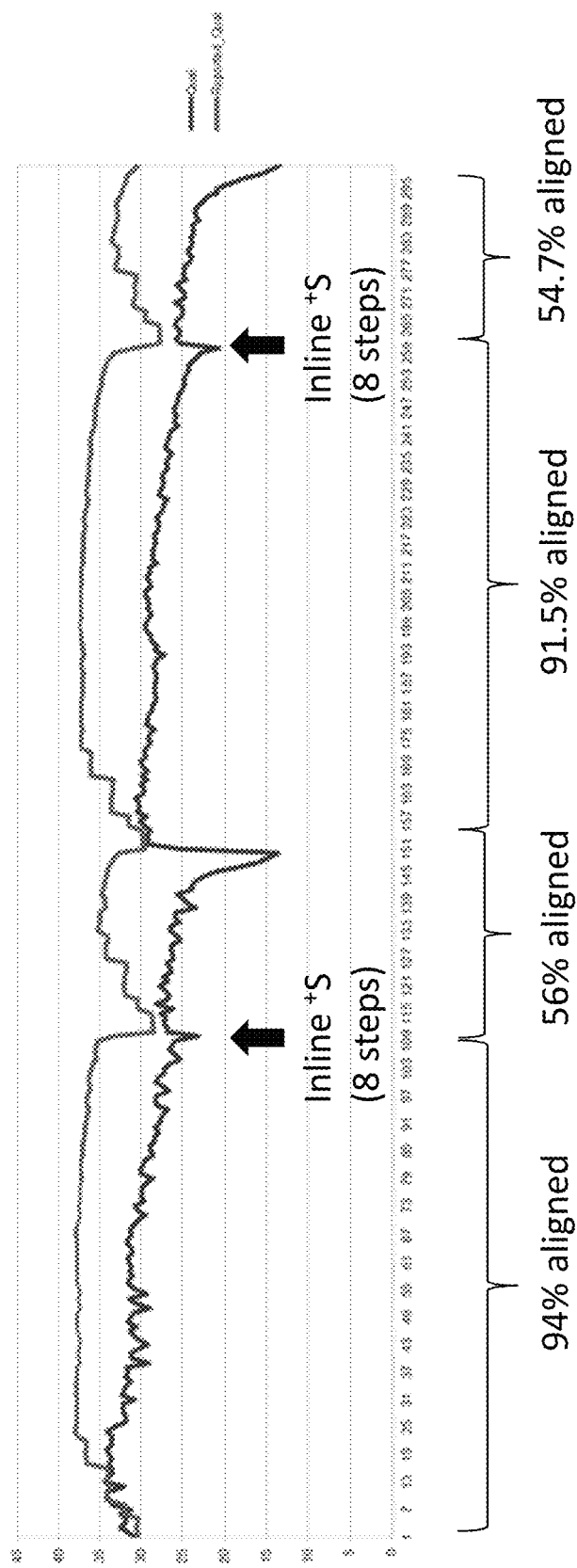
FIG. 13 depicts an increase in signal intensity utilizing the methods described herein.

Example 2—Inline +S Synchronization Resets Sequencing Strands after 110 Rounds of SBS Sequencing FIGS. 12 & 13 depict the results of a synchronization protocol. Briefly, sequencing-by-synthesis (SBS) reactions were performed on a MiSeq sequencing system (Illumina). After 110 rounds of SBS sequencing, the reactions were deblocked and the reactions were primed with apyrase followed by Mix0 at 37 C. Next, 8 inline +S synchronization steps were performed as follows: (-A, -C, -G, -T, -G, -C, -A, -T) to reset the sequencing strands. The synchronization protocol was followed by 40 rounds of sequencing. The sequencing and synchronization protocol was then repeated starting from the opposite end of the sequencing product. FIG. 12 depicts the intensity signal measured for each nucleotide (y-axis) at each step (x-axis). The first inline +S protocol resulted in a 12.2% average intensity increase (A: 15.0%, C: 8.2%, G: 17.0%, and T: 7.5%), whereas the second inline +S protocol resulted in an 11.5% average intensity increase (A: 15.5%, C: 4.6%, G: 20.0%, and T: 6.0%). FIG. 13 depicts the quality score (y-axis) of the sequencing reads at each step (x-axis). FIG. 13 compares the reported Illumina quality score calculated by algorithm (black line) with the quality score calculated by aligning the data to a reference sequence (grey line).

Example 3—Inline +S Synchronization Decreases the Error Rate of SBS Sequencing

Figure 14:
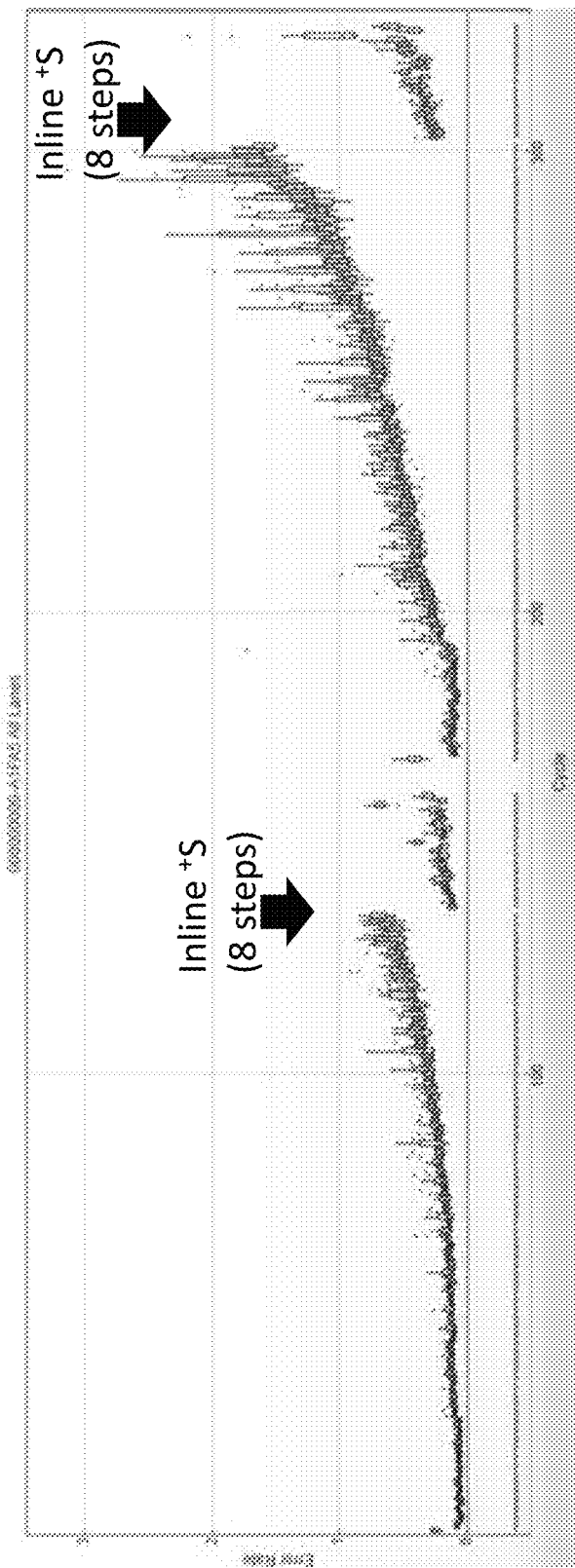
FIG. 14 depicts an increase in chastity score utilizing the methods described herein.
Figure 15:
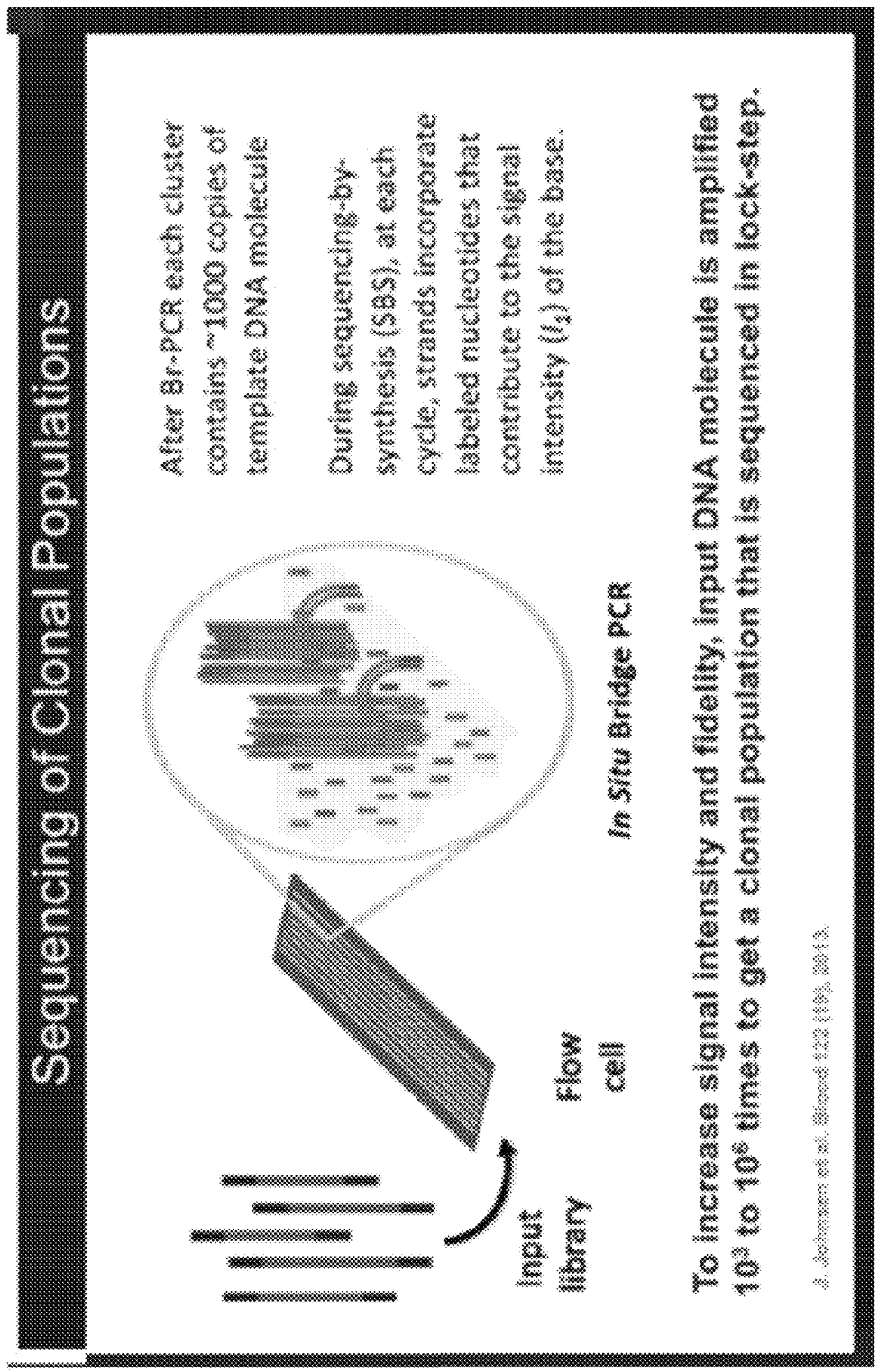
FIG. 15 depicts a method of sequencing clonal populations.
Figure 16:
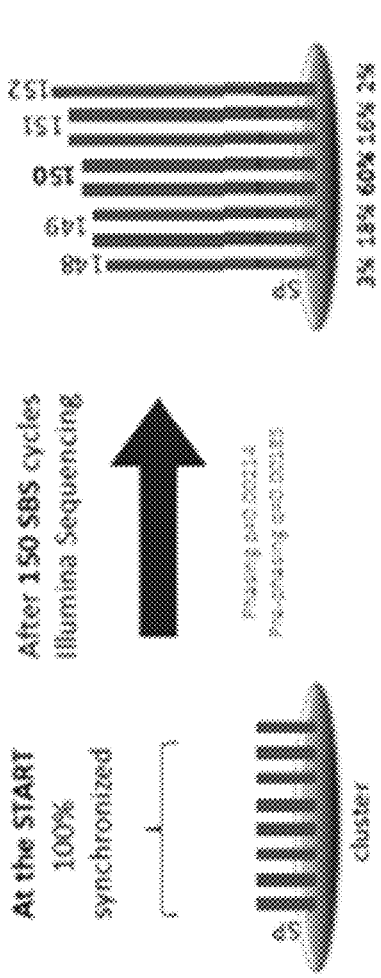
FIG. 16 depicts modeling of phasing effects in long reads.
Figure 17:
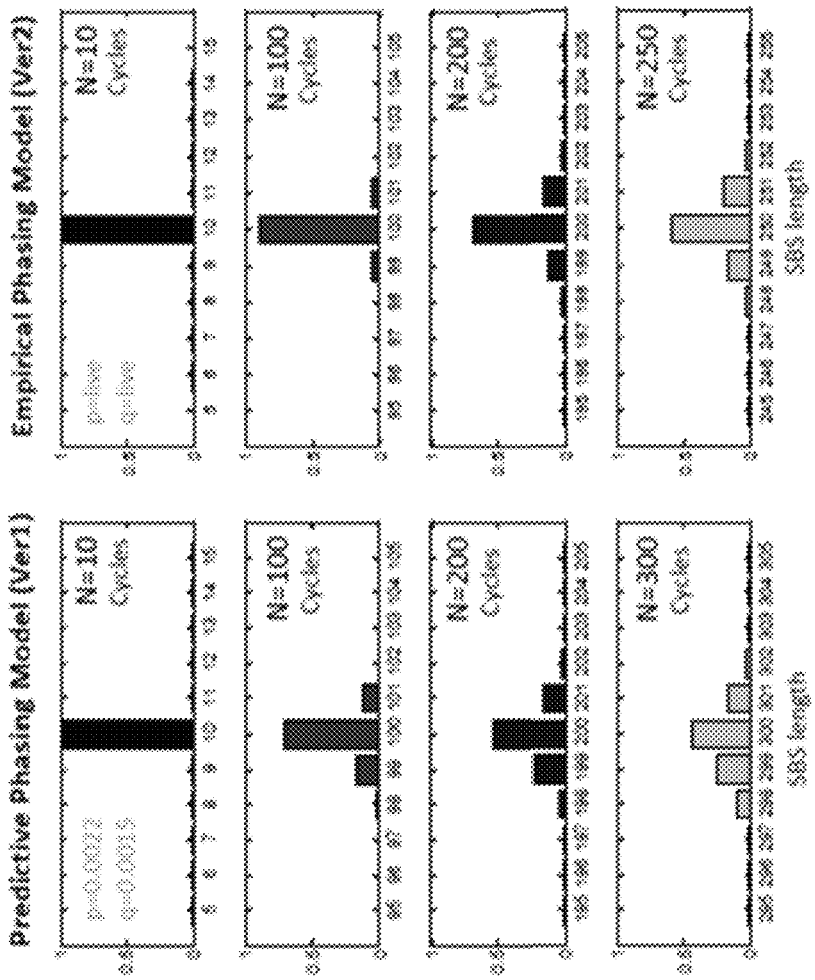
FIG. 17 depicts modeling of phasing effects in long reads.
Figure 18:
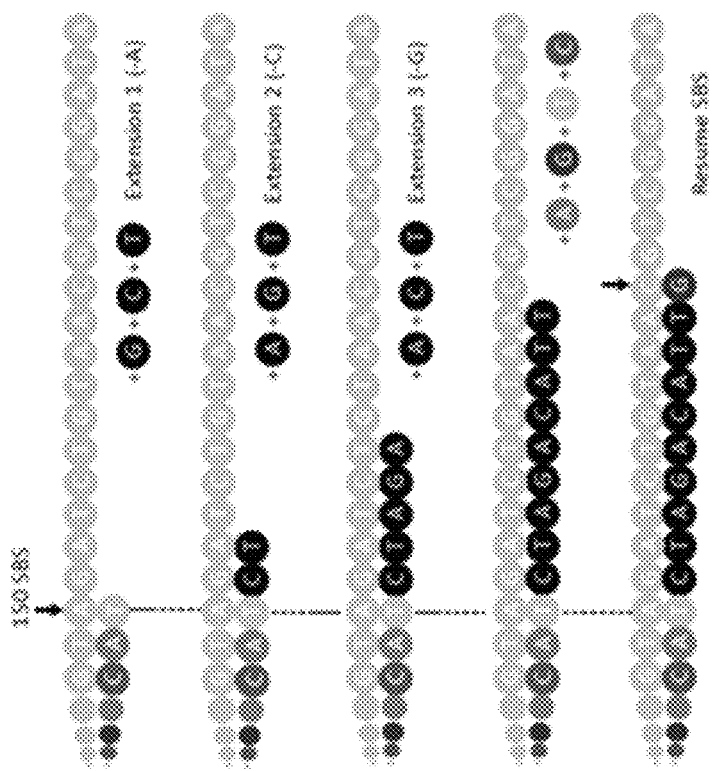
FIG. 18 depicts an example of a method described herein.
Figure 19:
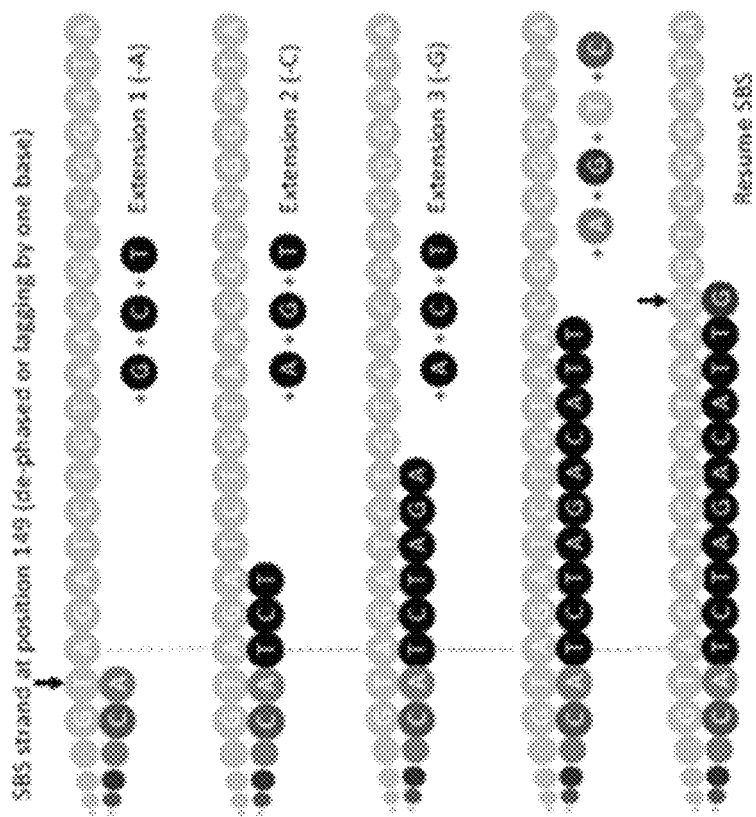
FIG. 19 depicts an example of a method described herein.
Figure 21:
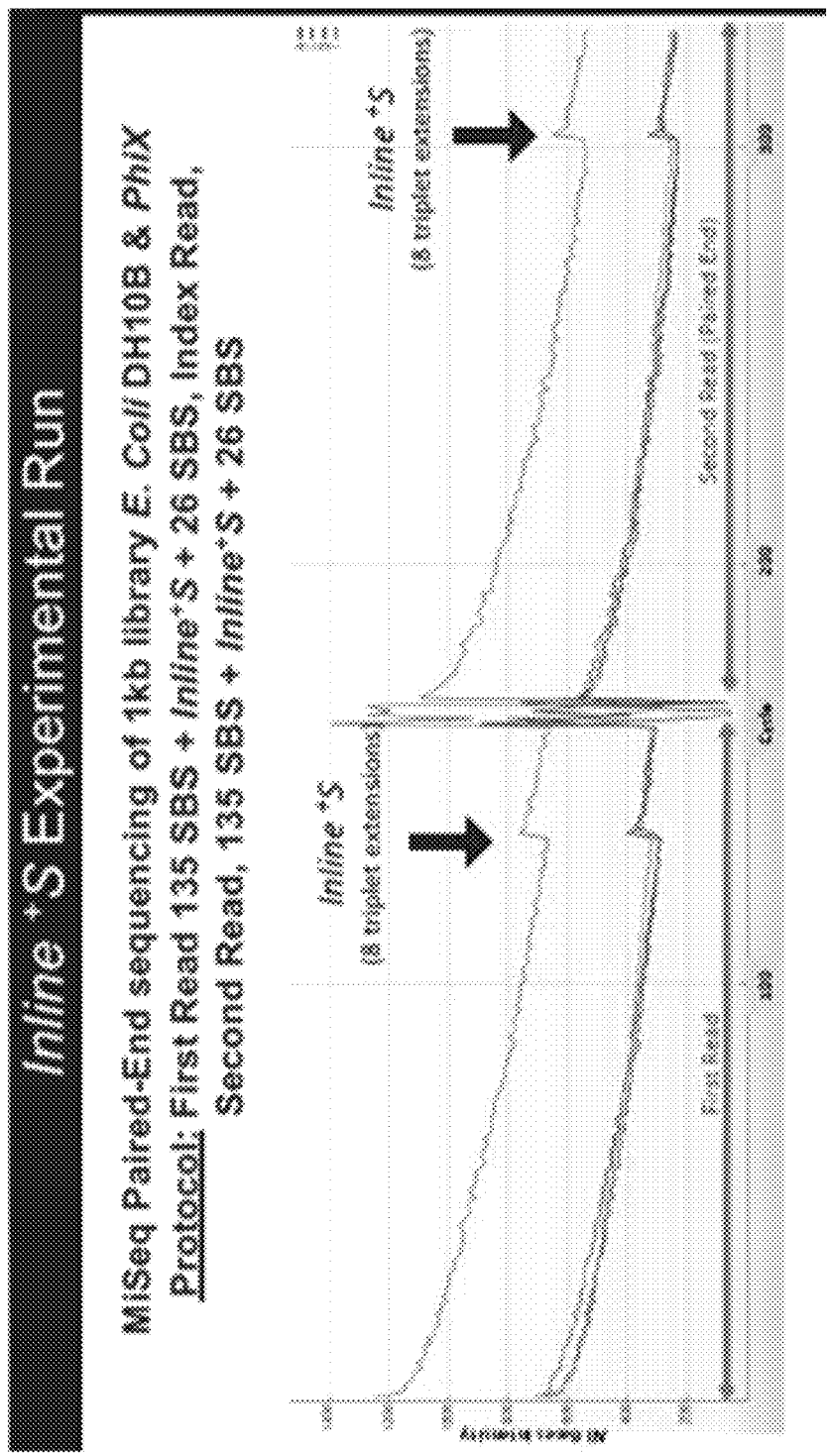
FIG. 21 depicts a result obtained from performing a method described herein.
Figure 22:
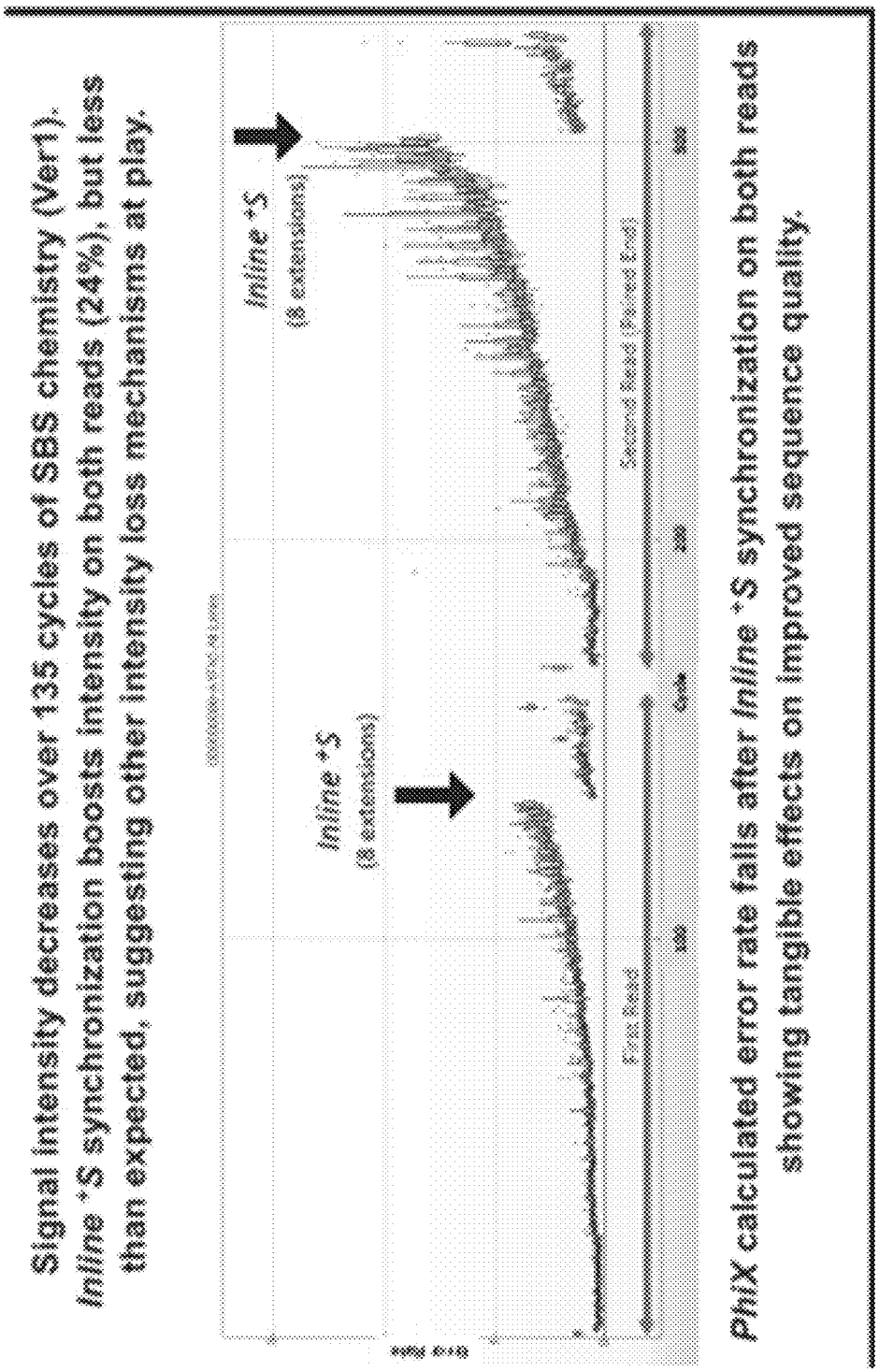
FIG. 22 depicts a result obtained from performing a method described herein.
Figure 23:
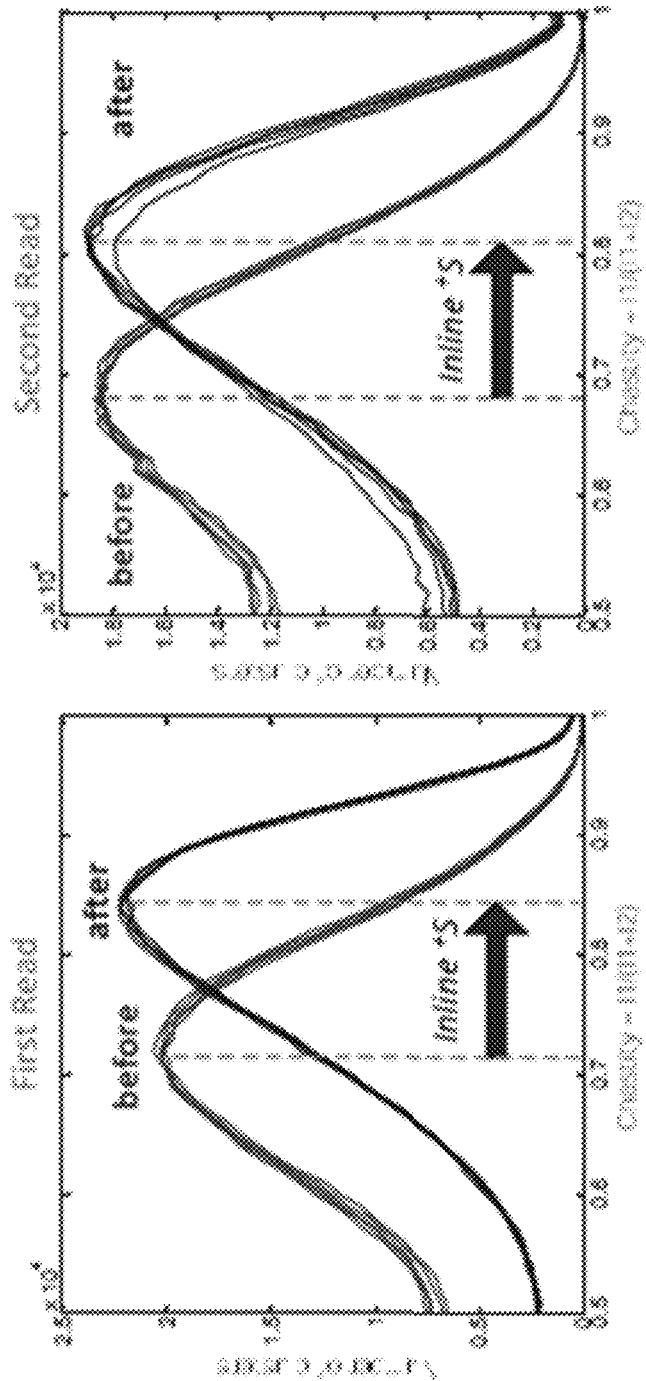
FIG. 23 depicts a result obtained from performing a method described herein.
Figure 24:
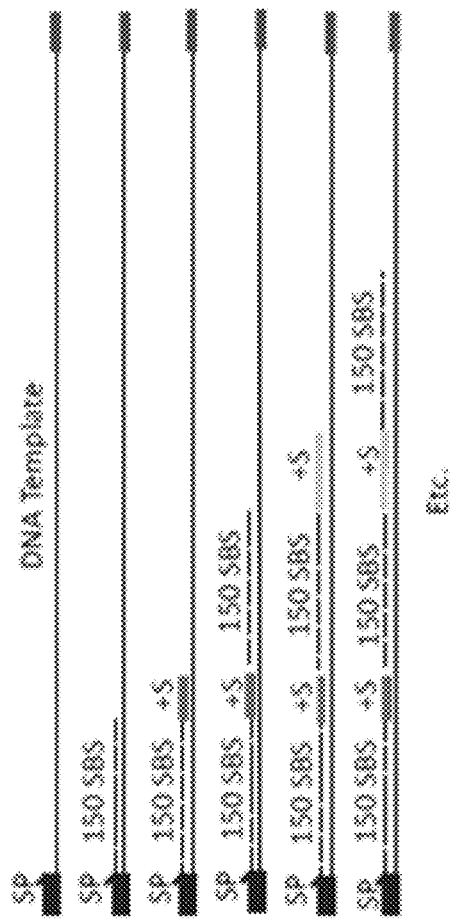
FIG. 24 depicts an example of a method described herein.

FIG. 14 depicts decreased error rates after implementing a synchronization protocol. Briefly, sequencing-by-synthesis (SBS) reactions on a PhiX sequencing control were performed using a MiSeq sequencing system (Illumina). After 110 rounds of SBS sequencing, the reactions were deblocked and the reactions were primed with apyrase followed by Mix0 at 37 C. Next, 8 inline +S synchronization steps were performed as follows: (-A, -C, -G, -T, -G, -C, -A, -T) to reset the sequencing strands. The synchronization protocol was followed by 40 rounds of sequencing. The sequencing and synchronization protocol was then repeated starting from the opposite end of the sequencing product.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of synchronizing one or more unsynchronized sequencing products, comprising:
   (a) hybridizing a plurality of sequencing primers to a plurality of target nucleic acids;
   (b) performing 50 or more successive rounds of sequencing, thereby producing a plurality of sequencing products comprising said one or more unsynchronized sequencing products; wherein each round of said 50 or more successive rounds of sequencing comprising:

extending said plurality of sequencing primers in the presence of one labeled nucleotide, and
(c) after said 50 or more successive rounds of sequencing, performing one or more synchronization steps on said plurality of sequencing products comprising said one or more unsynchronized sequencing products, wherein each of said one or more synchronization steps comprise:
  (i) contacting said plurality of sequencing products comprising said one or more unsynchronized sequencing products with a first set of three different unlabeled nucleotides selected from the group consisting of: dATP, dTTP, dCTP, dGTP and dUTP;
  (ii) extending said plurality of sequencing products comprising said one or more unsynchronized sequencing products with a DNA polymerase to produce a plurality of extended sequencing products; and
  (iii) optionally, removing said first set of three different nucleotides, thereby synchronizing said one or more unsynchronized sequencing products.

2. The method of claim 1, wherein said one or more synchronization steps further comprise: contacting said plurality of extended sequencing products with a second set of three different unlabeled nucleotides selected from the group consisting of: dATP, dTTP, dCTP, dGTP and dUTP, wherein said second set of unlabeled nucleotides is different from said first set of three different unlabeled nucleotides.

3. The method of claim 1, wherein said first set of three different unlabeled nucleotides comprises a reversible terminator nucleotide.

4. The method of claim 3, wherein after each synchronization step of said one or more synchronization steps, said reversible terminator nucleotide is deblocked and said plurality of sequencing products are made ready for further extension.

5. The method of claim 1, wherein, after performing said one or more synchronization steps, at least 95% of said plurality of extended sequencing products are synchronized.

6. The method of claim 1, wherein, after performing said one or more synchronization steps, said plurality of extended sequencing products having a chastity score of at least 0.85.

7. The method of claim 1, further comprising, removing said first set of three different nucleotides (i) by washing or (ii) by the use of a nucleotide degrading enzyme.

8. A method of synchronizing one or more unsynchronized sequencing products, comprising:
  performing one or more synchronization steps on a plurality of sequencing products, said plurality of sequencing products comprising said one or more unsynchronized sequencing products, wherein each of said one or more synchronization steps comprises:
  (i) contacting said plurality of sequencing products with a set of up to three different nucleotides selected from the group consisting of: dATP, dTTP, dCTP, dGTP and dUTP;
  (ii) extending said plurality of sequencing products with a DNA polymerase; and
  (iii) optionally, removing said set of up to three different nucleotides,
  thereby synchronizing said one or more unsynchronized sequencing products;
  wherein said one or more synchronization steps comprises eight consecutive synchronization steps, said eight consecutive synchronization steps comprising:
  contacting said plurality of sequencing products with dCTP, dGTP and dTTP;
  contacting said plurality of sequencing products with dATP, dTTP, and dGTP;
  contacting said plurality of sequencing products with dATP, dCTP, and dTTP;
  contacting said plurality of sequencing products with dATP, dCTP and dGTP;
  contacting said plurality of sequencing products with dATP, dCTP, and dTTP;
  contacting said plurality of sequencing products with dATP, dTTP, and dGTP;
  contacting said plurality of sequencing products with dCTP, dGTP and dTTP; and
  contacting said plurality of sequencing products with dATP, dCTP and dGTP.

9. The method of claim 8, further comprising, prior to performing said one or more synchronization steps, performing one or more successive rounds of sequencing.

10. The method of claim 9, wherein said one or more successive rounds of sequencing comprise 50 or more successive rounds of sequencing.

11. The method of claim 9, wherein each of said one or more successive rounds of sequencing comprises (i) extending a plurality of sequencing primers using a plurality of target nucleic acids as template in the presence of one or more labeled nucleotides to generate said plurality of sequencing products; and (ii) determining nucleic acid sequences of said plurality of sequencing products.

12. The method of claim 11, wherein said one or more labeled nucleotides comprise fluorescent labels.

13. The method of claim 11, wherein said plurality of target nucleic acids comprises DNA, RNA or modified nucleic acids.

14. The method of claim 11, wherein said plurality of target nucleic acids comprises at least 100,000 target nucleic acids.

15. The method of claim 8, further comprising, after performing said one or more synchronization steps, repeating, one or more times, one or more rounds of sequencing followed by one or more synchronization steps.

16. The method of claim 8, wherein said set of up to three different nucleotides comprises native nucleotides.

17. The method of claim 8, wherein said set of up to three different nucleotides comprises unlabeled nucleotides.

* * * * *

SEQUENCE LISTING

<160> NUMBER OF SEQ ID NOS: 16

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
acgtacgtac gt                                                           12

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
acgtacgtac gtacgt                                                       16

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggctctcaag ggca                                                         14

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggctctcaag ggcatcggtc g                                                 21

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggctctcaag ggcatcggtc gacgc                                             25

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggctctcaag ggcatcggtc gacgctctcc cttat                              35

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggctctcaag ggcatcggtc gacgctctcc cttatgcgac                         40

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggctctcaag ggcatcggtc gacgctctcc cttatgcgac tcctgc                  46

<210> SEQ ID NO 9
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggctctcaag ggcatcggtc gacgctctcc cttatgcgac tcctgcatta ggaag        55

<210> SEQ ID NO 10
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggctctcaag ggcatcggtc gacgctctcc cttatgcgac tcctgcatta ggaagcagcc   60
cag                                                                 63

<210> SEQ ID NO 11
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggctctcaag ggcatcggtc gacgctctcc cttatgcgac tcctgcatta ggaagcagcc   60

```
cagtagtagg ttgagg                                                    76

<210> SEQ ID NO 12
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggctctcaag ggcatcggtc gacgctctcc cttatgcgac tcctgcatta ggaagcagcc   60
cagtagtagg ttgaggccgt tg                                             82

<210> SEQ ID NO 13
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
ggctctcaag ggcatcggtc gacgctctcc cttatgcgac tcctgcatta ggaagcagcc   60
cagtagtagg ttgaggccgt tgagcaccgc cgccgcaagg aa                      102

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtagatctgt aacgtcggat a                                              21

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ttacagatct ac                                                        12

<210> SEQ ID NO 16
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gttacagatc tac                                                       13
```